(12) United States Patent
Leahy et al.

(10) Patent No.: US 10,640,482 B2
(45) Date of Patent: May 5, 2020

(54) SYNTHESIS OF CANNABINOIDS

(71) Applicant: University of South Florida, Tampa, FL (US)

(72) Inventors: James William Leahy, Lutz, FL (US); Zachary Paul Shultz, Temple Terrace, FL (US); Grant Alexander Lawrence, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/024,368

(22) Filed: Jun. 29, 2018

(65) Prior Publication Data

US 2019/0023680 A1 Jan. 24, 2019

Related U.S. Application Data

(60) Provisional application No. 62/535,388, filed on Jul. 21, 2017.

(51) Int. Cl.
| | | |
|---|---|---|
| *C07D 311/80* | (2006.01) | |
| *C07C 29/132* | (2006.01) | |
| *C07C 29/143* | (2006.01) | |
| *C07C 37/055* | (2006.01) | |
| *C07C 41/26* | (2006.01) | |
| *C07C 41/30* | (2006.01) | |
| *C07C 45/41* | (2006.01) | |
| *C07C 45/45* | (2006.01) | |
| *C07C 45/67* | (2006.01) | |
| *C07C 45/68* | (2006.01) | |
| *C07C 45/74* | (2006.01) | |
| *C07C 49/248* | (2006.01) | |
| *C07C 51/09* | (2006.01) | |
| *C07C 59/64* | (2006.01) | |
| *C07C 67/00* | (2006.01) | |
| *C07C 67/08* | (2006.01) | |
| *C07C 67/333* | (2006.01) | |
| *C07C 69/533* | (2006.01) | |
| *C07C 69/734* | (2006.01) | |

(52) U.S. Cl.
CPC .......... *C07D 311/80* (2013.01); *C07C 29/132* (2013.01); *C07C 29/143* (2013.01); *C07C 37/055* (2013.01); *C07C 41/26* (2013.01); *C07C 41/30* (2013.01); *C07C 45/41* (2013.01); *C07C 45/455* (2013.01); *C07C 45/673* (2013.01); *C07C 45/68* (2013.01); *C07C 45/74* (2013.01); *C07C 49/248* (2013.01); *C07C 51/09* (2013.01); *C07C 59/64* (2013.01); *C07C 67/00* (2013.01); *C07C 67/08* (2013.01); *C07C 67/333* (2013.01); *C07C 69/533* (2013.01); *C07C 69/734* (2013.01); *C07B 2200/07* (2013.01); *C07C 2601/16* (2017.05)

(58) Field of Classification Search
None
See application file for complete search history.

(56) References Cited

U.S. PATENT DOCUMENTS

| | | | |
|---|---|---|---|
| 3,734,930 | A | 5/1973 | Razdan et al. |
| 5,227,537 | A | 7/1993 | Stoss et al. |
| 7,572,928 | B2 | 8/2009 | Gouverneur |
| 2011/0263878 | A1 | 10/2011 | Burdick et al. |

FOREIGN PATENT DOCUMENTS

| | | |
|---|---|---|
| WO | 2002/096899 A1 | 12/2002 |
| WO | 2017/011210 A1 | 1/2017 |

OTHER PUBLICATIONS

Schafroth, M. A. et al. Angewandte Chemie, International Edition, 53(50), 13898-13901; 2014 (Year: 2014).*
Trost, B. M. et al. Org. Lett., vol. 9, No. 5, 2007, 861-863 (Year: 2007).*
Song, Y. et al. "Stereoselective Total Synthesis of (−)-Perrottetinene and Assignment of its Absolute Configuration" Org. Lett., vol. 10, No. 2, 2008, 269-271 (Year: 2008).*
Kurti, L. et al. "Strategic Applications of Named Reactions" Elseiver Academic Press, 2005, pp. 1-810 (Year: 2005).*
Andries et al., "Dronabinol in severe, enduring anorexia nervosa: a randomized controlled trial," International Journal of Eating Disorders, 2014, 47(1): 18-23.
Appendino et al., "Antibacterial Cannabinoids from Cannabis sativa: A Structure—Sctivity Study," Journal of Natural Products, 2008, 71, 1427-1430.
Atakan, "Cannabis, a complex plant: different compounds and different effects on individuals," Ther. Adv. Psychopharmacol., 2012, 2(6): 241-254.
Ballerini et al., "High-Pressure Diels-Alder Cycloadditions between Benzylideneacetones and 1,3-Butadienes: Application to the Synthesis of (R,R)-(−)- and (S,S)-(+)-Δ8-Tetrahydrocannabinol," J. Org. Chem., 2010, 75(12): 4251-4260.
Brand et al., "Cannabis in Chinese Medicine: Are Some Traditional Indications Referenced in Ancient Literature Related to Cannabinoids?," Front. Pharmacol., 2017, 8, 108, 11 pages.
Brimioulle et al., "Enantioselective Lewis acid catalysis of intramolecular enone [2+2] photocycloaddition reactions," Science, 2013, 342(6160): 840-3.
Campbell et al., "Are cannabinoids an effective and safe treatment option in the management of pain? A qualitative systematic review," BMJ, 2001, 323(7303): 1-6.
Capewell et al., "Diagnosis, Clinical Course, and Treatment of Primary Amoebic Meningoencephalitis in the United States, 1937-2013," J. Pediatric Infect Dis Soc., 2015, 4(4): e68-75.
Choi et al., "NMR assignments of the major cannabinoids and cannabiflavonoids isolated from flowers of Cannabis sativa," Phytochem. Anal, 2004, 15(6): 345-54.

(Continued)

*Primary Examiner* — Medhanit W Bahta
(74) *Attorney, Agent, or Firm* — Fish & Richardson P.C.

(57) ABSTRACT

Provided are synthesis processes and intermediates for preparing cannabinoids and analogs.

12 Claims, No Drawings

(56) References Cited

OTHER PUBLICATIONS

Compton et al., "Cannabinoid structure-activity relationships: correlation of receptor binding and in vivo activities," J. Pharmacol. Exp. Ther., 1993, 265(1): 218-26.
Contis-Montes de Oca et al., "Neutrophils extracellular traps damage Naegleria fowleri trophozoites opsonized with human IgG," Parasite Immunol., 2016, 38(8): 481-95.
Corey et al., "A stable and easily prepared catalyst for the enantioselective reduction of ketones. Applications to multistep syntheses," J. Am. Chem. Soc., 1987, 109(25): 7925-7926.
Corey et al., "Reduction of Carbonyl Compounds with Chiral Oxazaborolidine Catalysts: A New Paradigm for Enantioselective Catalysis and a Powerful New Synthetic Method," Angew. Chem., Int. Ed., 1998, 37(15): 1986-2012.
CTV News. Canadian Researchers to Study Cannabis Oil to Treat Kids' Epilepsy. http://www.ctvnews.ca/lifestyle/canadian-researchers-to-study-cannabis-oil-to-treat-kids-epilepsy-1.3321008 (accessed Jul. 23, 2017).
Dethe et al., "Protecting group free enantiospecific total syntheses of structurally diverse natural products of the tetrahydrocannabinoid family," Chem. Commun., 2015, 51(14): 2871-3.
Gaoni et al., "Isolation, Structure, and Partial Synthesis of an Active Constituent of Hashish," Journal of the American Chemical Society, 1964, 86(8): 1646-1647.
George Washington Grew Hemp. http://www.mountvernon.org/george-washington/the-man-the-myth/george-washington-grew-hemp (accessed Jul. 23, 2017).
Grubbs, "Olefin-metathesis catalysts for the preparation of molecules and materials (Nobel Lecture)," Angew. Chem., Int. Ed. Engl., 2006, 45(23): 3760-5.
Hanus et al., "Enantiomeric cannabidiol derivatives: synthesis and binding to cannabinoid receptors," Org. Biomol. Chem., 2005, 3(6): 1116-23.
Hua et al., "Crystal Structure of the Human Cannabinoid Receptor CB1," Cell, 167(3): 750-762.
Ireland et al., "Stereochemical control in the ester enolate Claisen rearrangement. 1. Stereoselectivity in silyl ketene acetal formation," J. Org. Chem., 1991, 56(2): 650-657.
Kauert et al., "Pharmacokinetic properties of delta-9-tetrahydrocannabinol in serum and oral fluid," Journal of Analytical Toxicology, 2007, 31, 288-293.

Kobayashi et al., "Synthesis of Cannabidiols via Alkenylation of Cyclohexenyl Monoacetate," Org. Lett., 2006, 8(13): 2699-2702.
Li, "An Archaeological and Historical Account of Cannabis in China," Econ. Bot., 1974, 28(4): 437-448.
Lipo et al., "The 'walking' megalithic statues (moai) of Easter Island," J. Archaeol. Sci., 2013, 40, 2859-2866.
Mackie et al., "Cannabinoid Receptors as Therapeutic Targets," Annual Review of Pharmacology and Toxicology 2006, 46, 101-122.
Makriyannis et al., "The molecular basis of cannabinoid activity," Life Sciences, 1990, 47(24): 2173-2184.
Mallipeddi et al., "Functional selectivity at G-protein coupled receptors: Advancing cannabinoid receptors as drug targets," Biochem. Pharmacol., 2017, 128: 1-11.
Martín Castro, "Claisen Rearrangement over the Past Nine Decades," Chem. Rev., 2004, 104(6): 2939-3002.
Padwa et al., "Utilization of the Intramolecular Cycloaddition-Cationic π-Cyclization of an Isomünchnone Derivative for the Synthesis of (±)-Lycopodine," J. Org. Chem., 1997, 62(1): 78-87.
Pertwee, "Cannabinoids and Multiple Sclerosis," Molecular Neurobiology, 2007, 36(1): 45-59.
Petrzilka et al., "Synthesis and optical rotation of the (−)-cannabidiols," Helv. Chim. Acta, 1967, 50(2): 719-23.
Pringle et al., "Susceptibility of Naegleria fowleri to delta 9-tetrahydrocannabinol," Antimicrob. Agents Chemother., 1979, 16(5): 674-9.
Ramos et al., "Therapeutic Potential of the Endocannabinoid System in the Brain," Mini-Reviews in Medicinal Chemistry, 2005, 5(7): 609-617.
Salzer et al., "Über neue synthetische, hochwirksame Östrogene," Physiol. Chem., 1942, 274, 39.
Schafroth et al., "Stereodivergent total synthesis of Δ9-tetrahydrocannabinols," Angew. Chem. Int. Ed. Engl., 2014, 126: 14118-14121.
Song et al., "Stereoselective total synthesis of (−)-perrottetinene and assignment of its absolute configuration," Org. Lett., 2008, 10(2): 269-71.
Stoss et al., "A Useful Approach Towards Δ9-Tetrahydrocannabinol," Synlett, 1991, 1991(8): 553-554.
U.S. Food and Drug Administration, "Marinol," https://www.accessdata.fda.gov/drugsatfda_docs/label/2005/018651s021lbl.pdf (accessed Jul. 23, 2017).
Ware et al., "A review of nabilone in the treatment of chemotherapy-induced nausea and vomiting," Therapeutics and Clinical Risk Management, 2008, 4(1): 99-107.

* cited by examiner

SYNTHESIS OF CANNABINOIDS

CROSS-REFERENCE TO RELATED APPLICATION(S)

This application claims the benefit of and priority to U.S. Provisional Patent Application No. 62/535,388, filed on Jul. 21, 2017, the entire content of which is incorporated herein by reference in its entirety.

FIELD

The present disclosure relates to synthesis methods for cannabinoids and analogues.

INTRODUCTION

Cannabinoids are compounds isolated from plants of the genus *Cannabis*, which are known for their psychotropic properties. There are more than 100 known cannabinoids present in varying amounts depending on the strain of the plant. The cannabinoids exert their physiological properties through their interaction with a series of receptors known as the cannabinoid receptors. Two of the primary cannabinoid receptors are CB1 and CB2, which are expressed in unique quantities in different tissues throughout the body. There is evidence that additional cannabinoid receptors exist, including GPR18 and GPR55. The overall biological response to *Cannabis* use is a composite of the interaction of the various cannabinoids with each of these receptors, such that different strains of *Cannabis* elicit different responses.

Two of the most abundant cannabinoids are $\Delta^9$-tetrahydrocannabinol (THC) and cannabidiol (CBD). Virtually any dispensary menu lists products with a percentage or weight of both of these components. Importantly, each compound has the ability to impact the effects of the other compound, leading to the subtly different responses to different products.

Given that different strains of *Cannabis* contain different amounts of each of the cannabinoids, it has proven quite difficult to conduct any serious clinical trials due in part to a lack of control over the exact amounts of the active ingredients. Further confounding this problem is the fact that the vast majority of the other cannabinoids have never been independently evaluated. Some of these minor cannabinoids are present in much smaller quantities than THC and CBD, which makes their isolation and study difficult. There is therefore a critical need for a practical synthetic approach to these molecules that will not only allow for them to be evaluated as single entities (or combined in easily reproduced ratios), but also for the generation of novel analogs that could have different biological and/or physicochemical properties.

SUMMARY

In one aspect, provided is process for the preparation of a compound of formula (I), a racemate or a stereoisomer thereof,

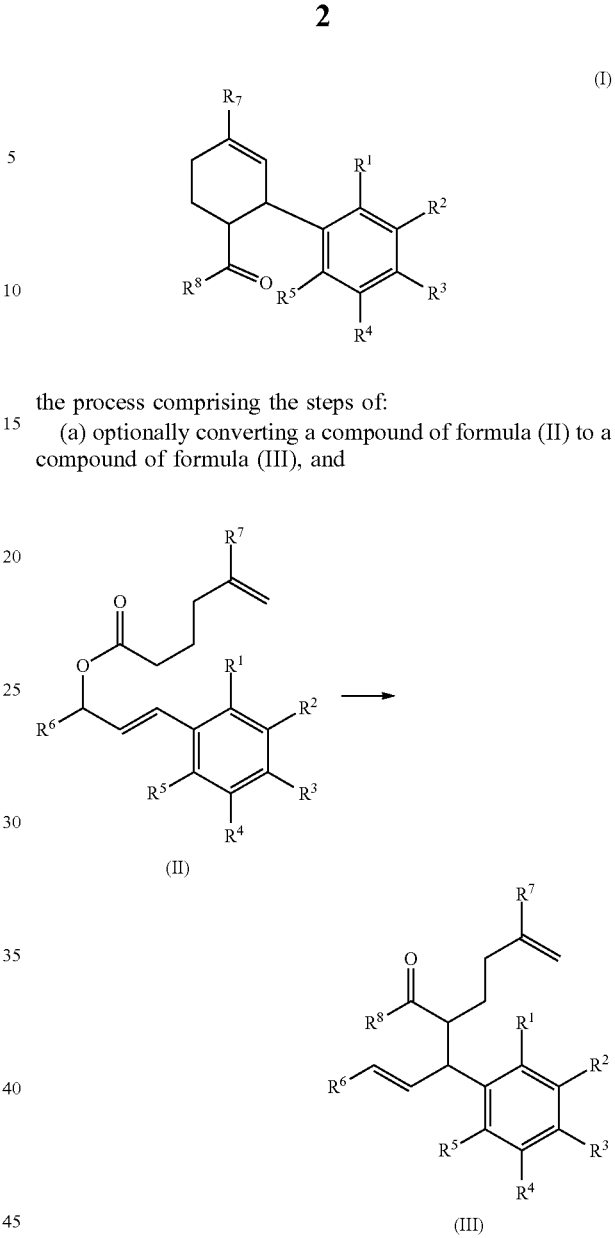

the process comprising the steps of:
  (a) optionally converting a compound of formula (II) to a compound of formula (III), and (b) converting the compound of formula (III) to the compound of formula (I), wherein
  $R^1$ and $R^5$ at each occurrence are independently hydroxyl or a protected hydroxyl group;
  $R^2$ and $R^4$ at each occurrence are independently hydrogen or $C_1$-$C_{10}$ alkyl;
  $R^3$ at each occurrence is independently $C_1$-$C_{10}$ alkyl;
  $R^6$ and $R^7$ at each occurrence are independently hydrogen or $C_1$-$C_{10}$ alkyl;
  $R^8$ at each occurrence is independently hydroxyl, $C_1$-$C_{10}$ alkyl, or $C_1$-$C_{10}$ alkoxy;
  wherein $R^2$, $R^3$, $R^4$, $R^6$, $R^7$, and $R^8$ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle.

In another aspect, provided is a compound of formula (II), a racemate or a stereoisomer thereof,

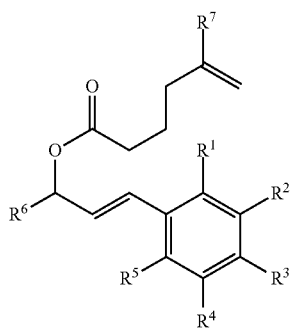

(II)

wherein

R¹ and R⁵ are independently hydroxyl or a protected hydroxyl group;

R² and R⁴ are independently hydrogen or $C_1$-$C_{10}$ alkyl;

R³ is $C_1$-$C_{10}$ alkyl; and

R⁶ and R⁷ are independently hydrogen or $C_1$-$C_{10}$ alkyl;

wherein R², R³, R⁴, R⁶, and R⁷ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle.

In another aspect, provided is a compound of formula (III), a racemate or a stereoisomer thereof,

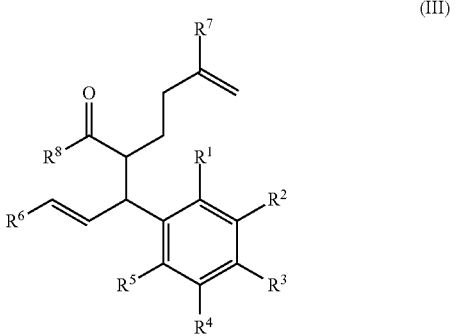

(III)

wherein

R¹ and R⁵ are independently hydroxyl or a protected hydroxyl group;

R² and R⁴ are independently hydrogen or $C_1$-$C_{10}$ alkyl;

R³ is $C_1$-$C_{10}$ alkyl;

R⁶ and R⁷ are independently hydrogen or $C_1$-$C_{10}$ alkyl; and

R⁸ is hydroxyl, $C_1$-$C_{10}$ alkyl, or $C_1$-$C_{10}$ alkoxy wherein R², R³, R⁴, R⁶, R⁷, and R⁸ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle.

Other aspects of the invention will become apparent by consideration of the detailed description and accompanying drawings. Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

DETAILED DESCRIPTION

Disclosed herein are processes for the synthesis of cannabinoids and their non-naturally occurring analogs. Also provided herein are synthetic intermediates useful in the processes disclosed herein.

1. Definitions

The use of "including," "comprising," "having" and variations thereof, as used herein, are meant to encompass the items listed thereafter and equivalents thereof as well as additional items. Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyl groups of the present invention may be unsubstituted or substituted by one or more suitable substituents, preferably 1 to 3 suitable substituents, as defined herein.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

As used herein, the term "alkyl" refers to a linear or branched hydrocarbon radical, preferably having 1 to 30 carbon atoms, 1 to 10 carbon atoms, 1 to 6 carbon atoms or 1 to 4 carbon atoms. The term "$C_1$-$C_4$-alkyl" is defined to include alkyl groups having 1, 2, 3, or 4 carbons in a linear or branched arrangement. For example, "$C_1$-$C_4$-alkyl" specifically includes methyl, ethyl, n-propyl, i-propyl, n-butyl, t-butyl, and i-butyl. The term "$C_1$-$C_6$-alkyl" is defined to include alkyl groups having 1, 2, 3, 4, 5 or 6 carbons in a linear or branched arrangement. For example, "$C_1$-$C_6$-alkyl" specifically includes methyl, ethyl, n-propyl, i-propyl, n-butyl, t-butyl, i-butyl, pentyl and hexyl.

As used herein, the term "alkylcarbonyl" refers to an alkyl group appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

As used herein, the term "alkylene" refers to a divalent group derived from a straight or branched chain hydrocarbon. Representative examples of alkylene include, but are not limited to, —$CH_2$—, —$CH_2CH_2$—, —$CH_2CH_2CH_2$—, —$CH_2CH(CH_3)CH_2$—, and —$CH_2CH(CH_3)CH(CH_3)CH_2$—.

As used herein, the term "arylalkyl" refers to an aryl group, as defined herein, appended to the parent molecular moiety through an alkyl group, as defined herein. In some embodiments, the alkyl group may be $C_1$-$C_4$-alkyl.

As used herein, the term "alkynyl" refers to a straight or branched hydrocarbon radical having 2, 3, 4, 5, 6, 7, 8, 9 or 10 carbons and having one or more carbon-carbon triple bonds. Alkynyl groups of the present invention include, but are not limited to, ethynyl, propynyl and butynyl. Alkynyl groups of the present invention may be unsubstituted or substituted by one or more suitable substituents, preferably 1 to 3 suitable substituents, as defined above. As used herein, the term "heteroarylalkyl" refers to a heteroaryl group, as defined herein, appended to the parent molecular moiety through an alkyl group, as defined here. In some embodiments, the alkyl group may be $C_1$-$C_4$-alkyl.

As used herein, the term "amino" refers to an —$NH_2$ group, optionally substituted with one or two $C_1$-$C_{10}$ alkyl groups.

As used herein, the term "aryl" refers to monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention may be optionally substituted by one or more suitable substituents, preferably 1 to 5 suitable substituents, as defined herein.

As used herein, the term "arylcarbonyl" refers to an aryl group, as defined herein, appended to the parent molecular moiety through a carbonyl group, as defined herein.

As used herein, the term "carbonyl" or "(C=O)" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxyl (C=O)—NH—) refers to an alkyl carbamate group. The carbonyl group is also equivalently defined herein as (C=O). Alkylcarbonylamino refers to groups such as acetamide.

As used herein, the term "carboxylic acid" refers to COOH.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups of the present invention may be unsubstituted or substituted by one or more suitable substituents, preferably 1 to 5 suitable substituents, as defined herein.

As used herein, the term "halogen" or "halo" refers to a fluoro, chloro, bromo or iodo radical.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups of the present invention may be unsubstituted or substituted by one or more suitable substituents, preferably 1 to 5 suitable substituents, as defined herein.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.13,7]decane. Heterocyclic groups of the present invention may be unsubstituted or substituted by one or more suitable substituents, preferably 1 to 3 suitable substituents, as defined above. Heterocyclic groups of the present invention may contain one or more oxo groups (=O) or thioxo (=S) groups attached to the ring.

As used herein, the term "hydroxyl" refers to an —OH group.

As used herein, the term "oxo" refers to a double bonded oxygen (=O) radical wherein the bond partner is a carbon atom. Such a radical can also be thought as a carbonyl group.

As used herein, the term "protected hydroxyl" refers to a hydroxyl group substituted with a suitably selected oxygen protecting group, which may be attached the oxygen atom of the hydroxyl to protect said oxygen atom from participating in a reaction and which may be readily removed following the reaction. Suitable oxygen protecting groups include, but are not limited to, methyl, acetyl, benzoyl, t-butyl-dimethylsilyl, trimethylsilyl (TMS), methoxymethyl (MOM and tetrahydropyranyl (THP). The oxygen protecting groups may be introduced and removed using methods known in the art, such as those described in T. W. Green, P. G. M. Wuts, *Protective Groups in Organic Synthesis*, Wiley-Interscience, 3$^{rd}$ Edition, 1999.

As used herein, the term "suitable substituent" is intended to mean a chemically acceptable functional group e.g., a moiety that does not negate the activity of the inventive compounds. Illustrative examples of suitable substituents include, but are not limited to, halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents.

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a substituent is referred to as "unsubstituted" or not referred to as "substituted" or "optionally substituted", it means that the substituent does not have any substituents. If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 nonhydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 nonhydrogen radical.

If substituents are described as being "independently selected" from a group, each substituent is selected independent of the other. Each substituent, therefore, may be identical to or different from the other substituent(s).

2. Synthesis Process

In one aspect, disclosed is a process for the preparation of a compound of formula (I), a racemate or a stereoisomer thereof,

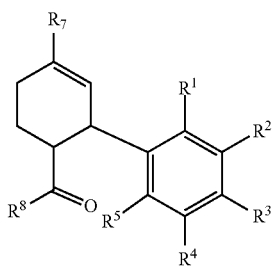
(I)

the process comprising the steps of:
(a) optionally converting a compound of formula (II) to a compound of formula (III), and

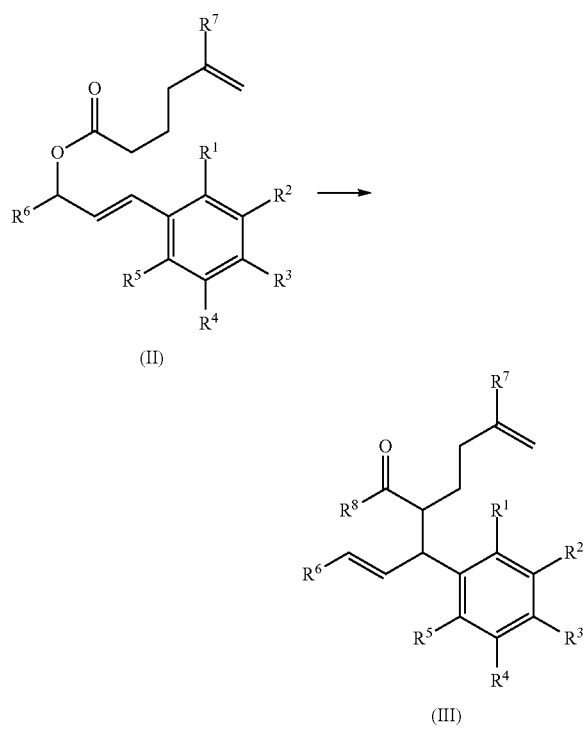
(II)

(III)

(b) converting the compound of formula (III) to the compound of formula (I), wherein
R$^1$ and R$^5$ at each occurrence are independently hydroxyl or a protected hydroxyl group;
R$^2$ and R$^4$ at each occurrence are independently hydrogen or C$_1$-C$_{10}$ alkyl;
R$^3$ at each occurrence is independently C$_1$-C$_{10}$ alkyl;
R$^6$ and R$^7$ at each occurrence are independently hydrogen or C$_1$-C$_{10}$ alkyl;
R$^8$ at each occurrence is independently hydroxyl, C$_1$-C$_{10}$ alkyl, or C$_1$-C$_{10}$ alkoxy;

wherein R$^2$, R$^3$, R$^4$, R$^6$, R$^7$, and R$^8$ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle.

In certain embodiments, R$^1$ and R$^5$ at each occurrence are independently —OCH$_3$ or other protected hydroxyl group, which can be deprotected by method known in the art.

In certain embodiments, R$^2$ and R$^4$ at each occurrence are independently hydrogen.

In certain embodiments, R$^3$ at each occurrence is C$_1$-C$_6$ alkyl, such as —(CH$_2$)$_4$—CH$_3$.

In certain embodiments, R$^6$ and R$^7$ at each occurrence are independently hydrogen or C$_1$-C$_4$ alkyl, such as —CH$_3$.

In certain embodiments, R$^8$ is hydroxyl, C$_1$-C$_4$ alkyl (such as —CH$_3$), or C$_1$-C$_4$ alkoxy (such as —OCH$_3$).

In certain embodiments, the compound of formula (I) is a compound of formula (I-a), wherein R$^1$, R$^2$, R$^3$, R$^4$, R$^5$, R$^7$, and R$^8$ are as defined above.

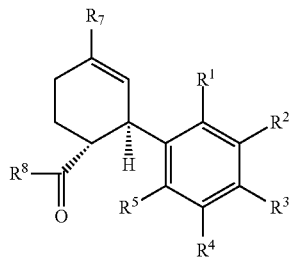
(I-a)

In certain embodiments, the present process includes step (a), in which a compound of formula (II) is converted to a compound of formula (III). In other embodiments, step (a) is absent, and an alternative synthetic route is employed to provide the compound of formula (III).

In certain embodiments, step (a) is present, and includes mixing an agent that assists the conversion of the compound of formula (II) to the compound of formula (III). In a particular embodiment, the agent is potassium bis(trimethylsilyl)amide (KHMDS). For example, step (a) includes mixing potassium bis(trimethylsilyl)amide (KHMDS) with the compound of formula (II), under conditions suitable for the production of the compound of formula (III).

In certain embodiments, the compound of formula (II) is a compound of formula (II-a), wherein R$^1$, R$^2$, R$^3$, R$^4$, R$^5$, R$^6$, and R$^7$ are as defined above.

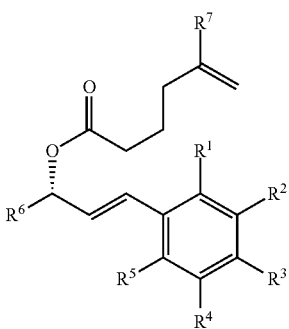
(II-a)

In certain embodiments, the compound of formula (III) is a compound of formula (III-a), wherein $R^1$, $R^2$, $R^3$, $R^4$, $R^5$, $R^6$, and $R^7$ are as defined above.

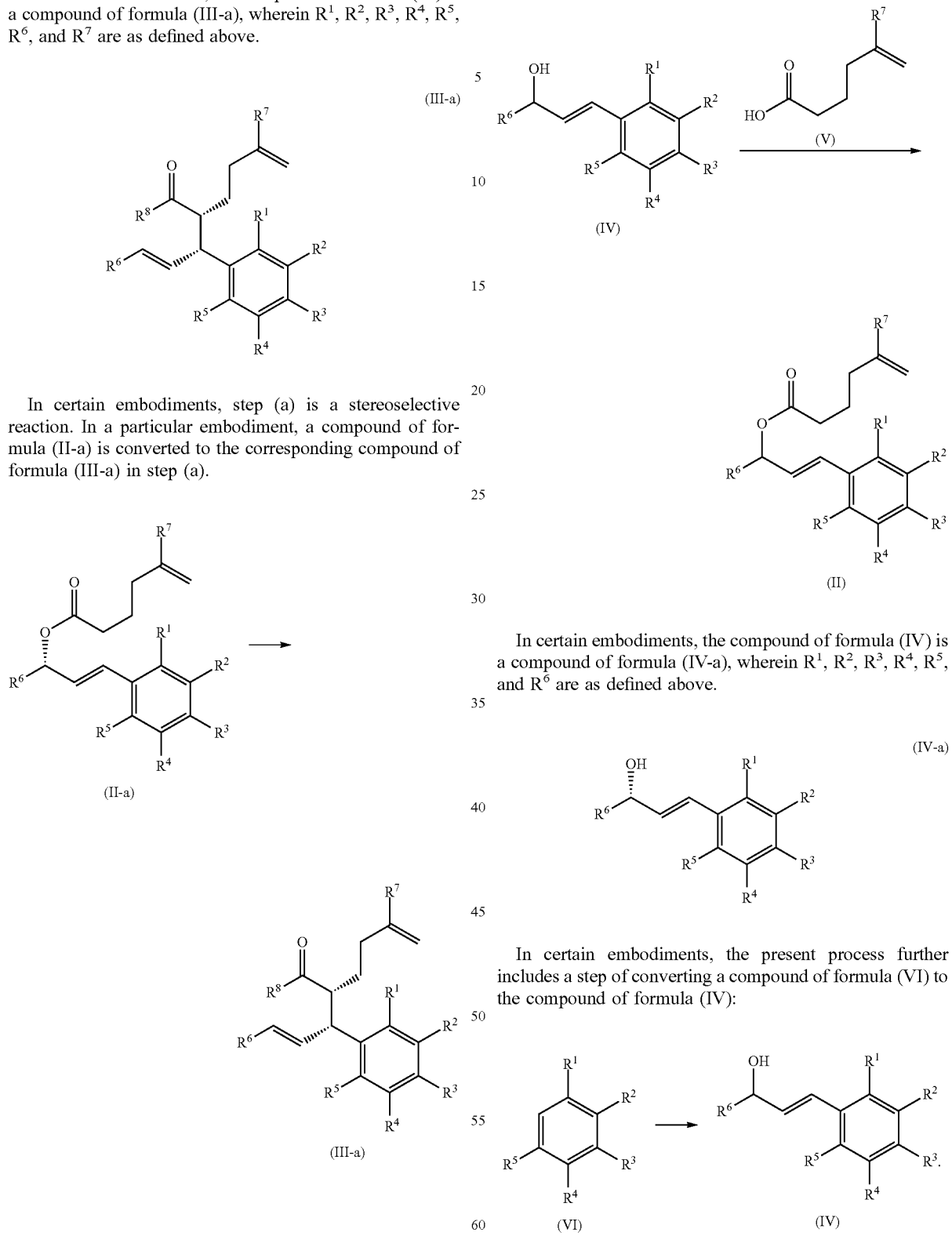

In certain embodiments, step (a) is a stereoselective reaction. In a particular embodiment, a compound of formula (II-a) is converted to the corresponding compound of formula (III-a) in step (a).

In certain embodiments, the compound of formula (IV) is a compound of formula (IV-a), wherein $R^1$, $R^2$, $R^3$, $R^4$, $R^5$, and $R^6$ are as defined above.

In certain embodiments, the present process further includes a step of converting a compound of formula (VI) to the compound of formula (IV):

In certain embodiments, the present process further includes a step of reacting a compound of formula (IV) with compound of formula (V) to produce the compound of formula (II), wherein $R^1$, $R^2$, $R^3$, $R^4$, $R^5$, $R^6$, and $R^7$ are as defined above.

In certain embodiments, the present process further includes a step of reacting the compound of formula (VI) first to a compound of formula (IV'), followed by a step of reducing the compound of formula (IV') to the compound of formula (IV):

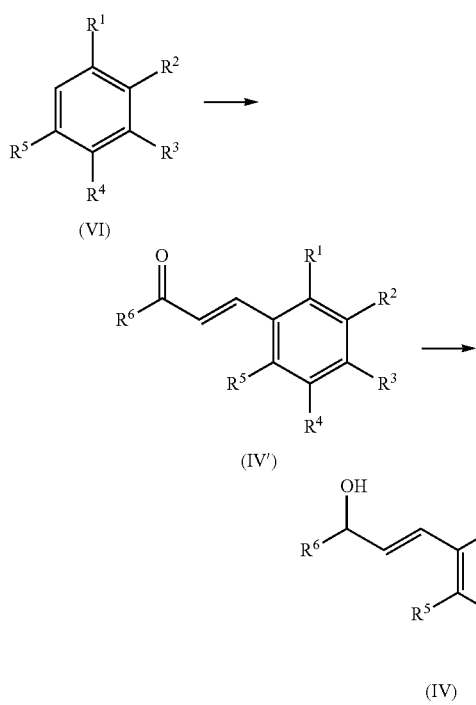

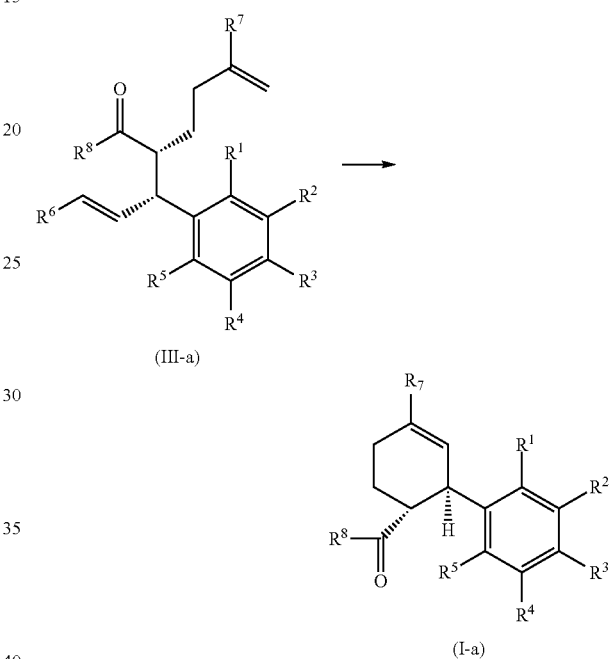

In certain embodiments, step (b) includes a catalyst that assists a ring closure process converting the compound of formula (III) to the corresponding compound of formula (I). In a particular embodiment, the catalyst is Grubbs' second generation catalyst, such as (1,3-bis(2,4,6-trimethylphenyl)-2-imidazolidinylidene)dichloro(phenylmethylene)(tricyclo-hexylphosphine)-ruthenium. For example, step (b) may include mixing the compound of formula (III) with (1,3-bis (2,4,6-trimethylphenyl)-2-imidazolidinylidene)dichloro (phenylmethylene)(tricyclohexylphos-phine)ruthenium.

In certain embodiments, the ring closure reaction of step (b) is a stereoselective reaction. In a particular embodiment, a compound of formula (III-a) is converted to the corresponding compound of formula (I-a) in step (b).

In certain embodiments, the reduction of the compound of formula (IV') to form the compound of formula (IV) is catalyzed by a chiral catalyst known in the art. In a particular embodiment, the catalyst is a borane reducing agent, such as those prepared from the Corey-Bakshi-Shibata (CBS) ligands. In certain embodiments, the reduction of the compound of formula (IV') is catalyzed by a chiral catalyst (such as CBS) resulting in the production of compound (IV-a).

In some embodiments, the reduction of the compound of formula (IV') is carried out in the absence of any chiral agents and produces a racemic mixture of compounds of formula (IV). Subsequently, compounds of formula (IV-a) or derivatives thereof may be produced from the racemic mixture of compounds of formula (IV) using enzymatic or non-enzymatic methods. For example, the compound of formula (IV') may be reduced by reagents (such as sodium borohydride) to provide a racemic alcohol of formula (IV), followed by acylation in the presence of an enzyme (such as Savinase 12T) to yield an ester with high enantiopurity (e.g. >98% ee).

In certain embodiments, the compound of formula (VI) may be a commercially available compound, such olivetol.

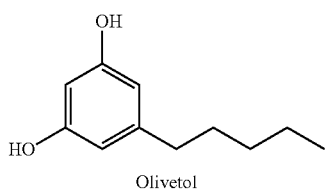
Olivetol

In certain embodiments, the synthesis of the compound of formula (IV') from the compound of formula (VI) may be carried out by methods known in the art. For example, such method may include introducing an aldehyde group and subsequent aldol condensation to provide the desired enone structure.

In certain embodiments, the present process may include an additional step of converting the $R^8$ group of the compound of formula (III) from a hydroxyl to a $C_1$-$C_{10}$ alkyl, or from a hydroxyl to a $C_1$-$C_{10}$ alkoxy before carrying out step (b) to form the corresponding compound of formula (I).

Compound of formula (I) may be used for the synthesis of cannabinoids and their non-naturally occurring analogs. In one aspect, a process for producing a cannabinoid or analogs thereof is provided herein, which includes converting a compound of formula (I) to a compound of formula (VII), wherein $R^1$, $R^2$, $R^3$, $R^4$, $R^5$, $R^7$, and $R^8$ are as defined above, and wherein $R^a$ and $R^b$ are each independently $C_1$-$C_{10}$ alkyl.

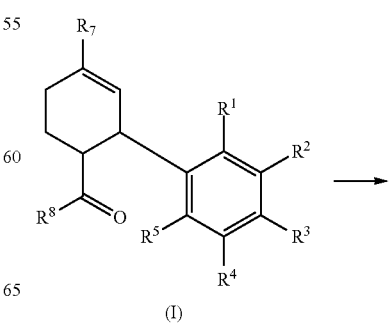

-continued

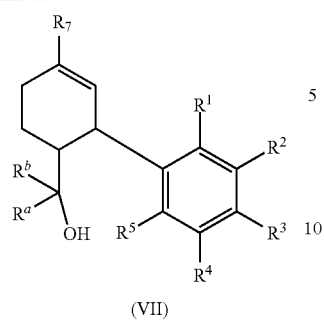

(VII)

For example, the compound of formula (I), in which $R^8$ is $C_1$-$C_{10}$ alkoxy, can be converted to the corresponding compound of formula (VII) by known methods (such as Grignard reactions). $R^a$ and $R^b$ may be the same or different. In some embodiments, the compound of formula (I) is a compound of formula (I-a), and the resulting compound of formula (VII) has the same stereochemistry as the compound of formula (I-a).

In a particular embodiment, the present process can be used to produce (−)-$\Delta^9$-tetrahydrocannabinol (THC) using a corresponding compound of formula (I-a), via a corresponding intermediate of formula (VII).

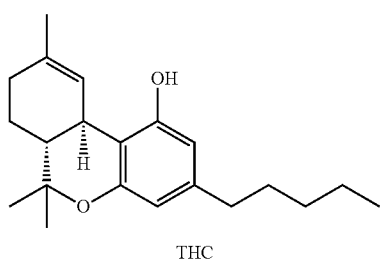

THC

In another aspect, a process for producing a cannabinoid or analogs thereof is provided herein, which includes converting a compound of formula (I) to a compound of formula (VIII), wherein $R^1$, $R^2$, $R^3$, $R^4$, $R^5$, $R^7$, and $R^8$ are as defined above.

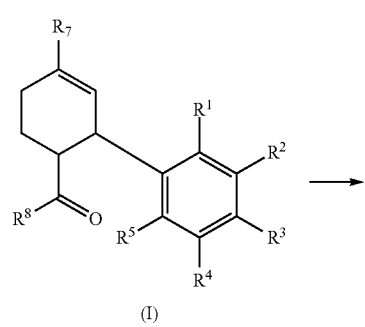

(I)

-continued

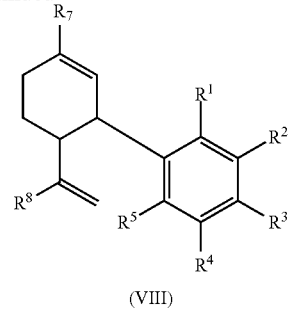

(VIII)

For example, the compound of formula (I), in which $R^8$ is $C_1$-$C_{10}$ alkyl, can be converted to the corresponding compound of formula (VIII) by known methods (such as Wittig olefination). In some embodiments, the compound of formula (I) is a compound of formula (I-a), and the resulting compound of formula (VIII) has the same stereochemistry as the compound of formula (I-a).

In a particular embodiment, the present process can be used to produce cannabidiol (CBD) using a corresponding compound of formula (I-a), via a corresponding intermediate of formula (VIII).

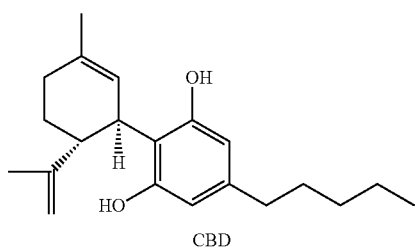

CBD

A non-limiting, representative route for preparing cannabinoids and analogs according to the process disclosed herein is shown in Scheme 1.

Scheme 1 Representative retrosynthetic pathway for preparing THC

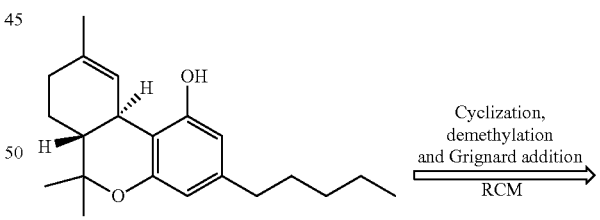

THC

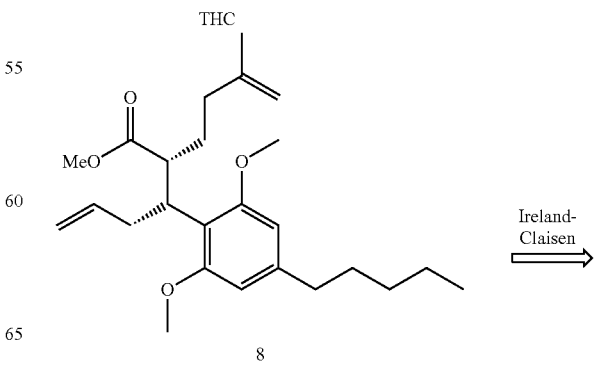

8

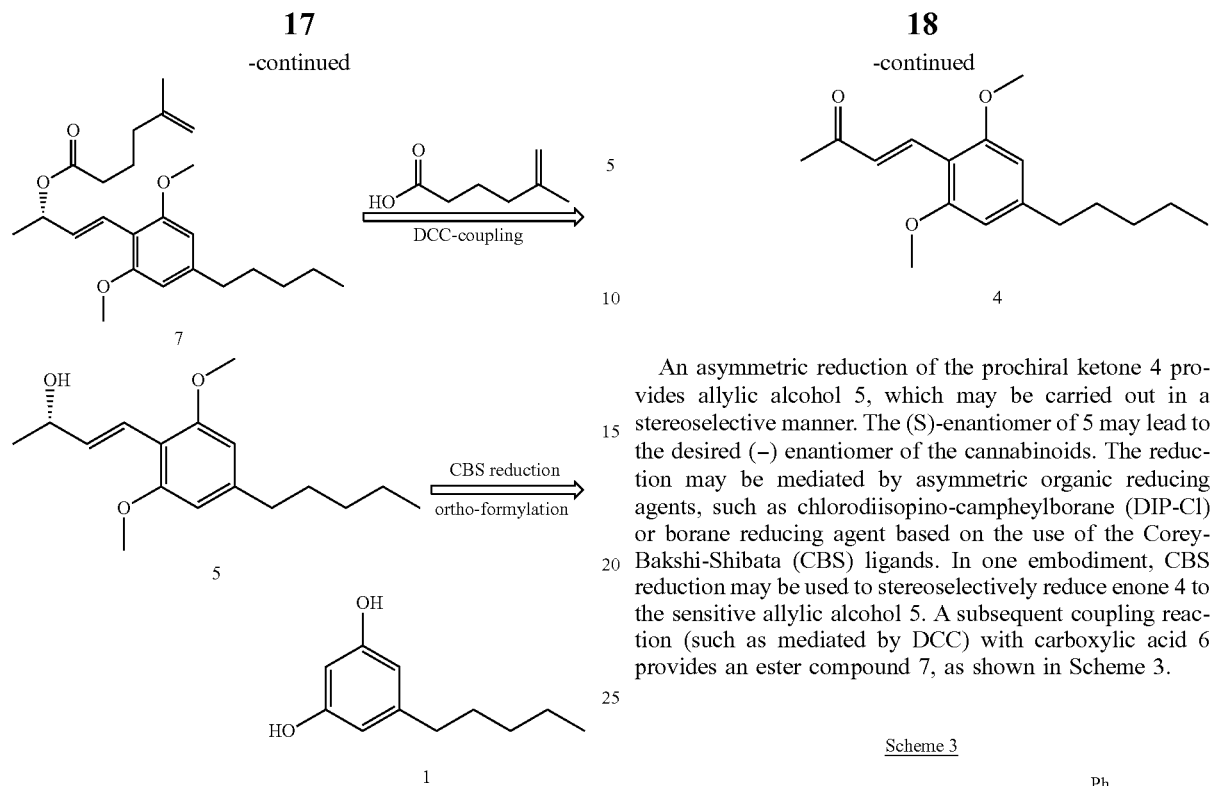

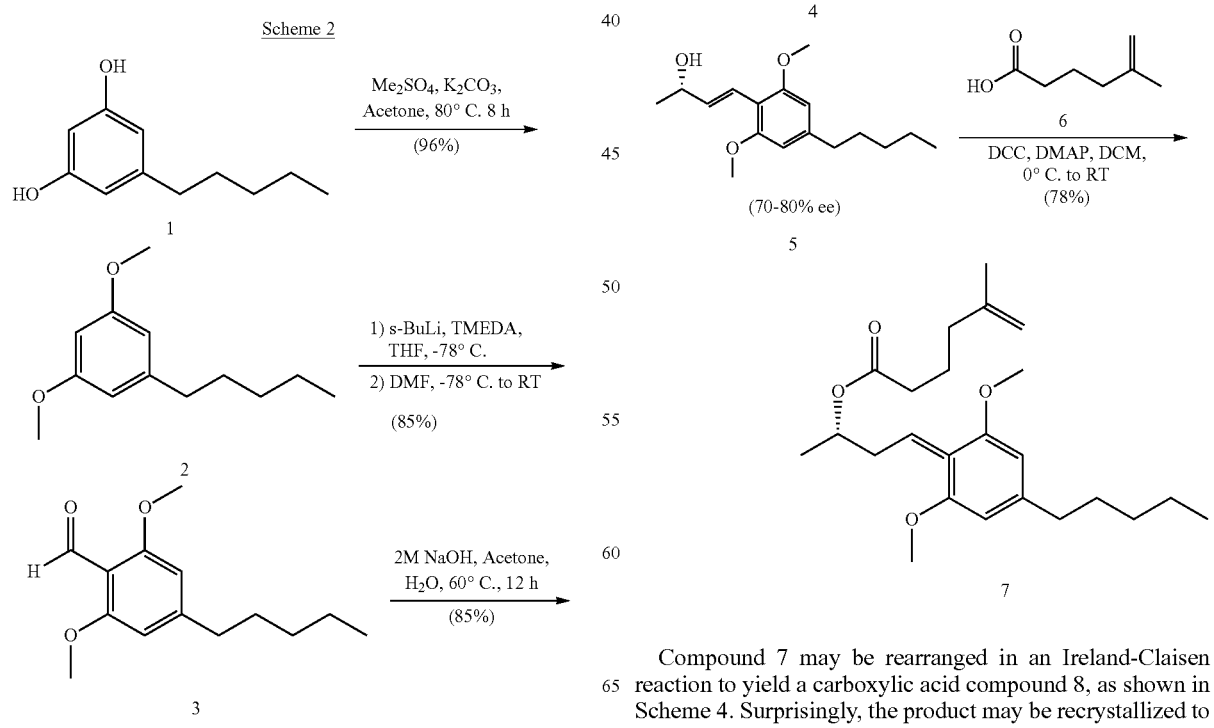

An asymmetric reduction of the prochiral ketone 4 provides allylic alcohol 5, which may be carried out in a stereoselective manner. The (S)-enantiomer of 5 may lead to the desired (−) enantiomer of the cannabinoids. The reduction may be mediated by asymmetric organic reducing agents, such as chlorodiisopino-campheylborane (DIP-Cl) or borane reducing agent based on the use of the Corey-Bakshi-Shibata (CBS) ligands. In one embodiment, CBS reduction may be used to stereoselectively reduce enone 4 to the sensitive allylic alcohol 5. A subsequent coupling reaction (such as mediated by DCC) with carboxylic acid 6 provides an ester compound 7, as shown in Scheme 3.

In a particular embodiment, commercially available olivetol 1 may be used to provide the desired allylic alcohol 5. For example, methyl protection of the bisphenol followed by ortho-lithiation and quenching with anhydrous DMF provides aldehyde 3. An aldol condensation with acetone and NaOH provides the desired enone 4, as shown in scheme 2.

Compound 7 may be rearranged in an Ireland-Claisen reaction to yield a carboxylic acid compound 8, as shown in Scheme 4. Surprisingly, the product may be recrystallized to provide a crystalline solid with high stereoselectivity, such as over 90% ee. The relative stereochemistry of the product 8 may be unequivocally determine the by single crystal X-ray crystallography.

Scheme 4

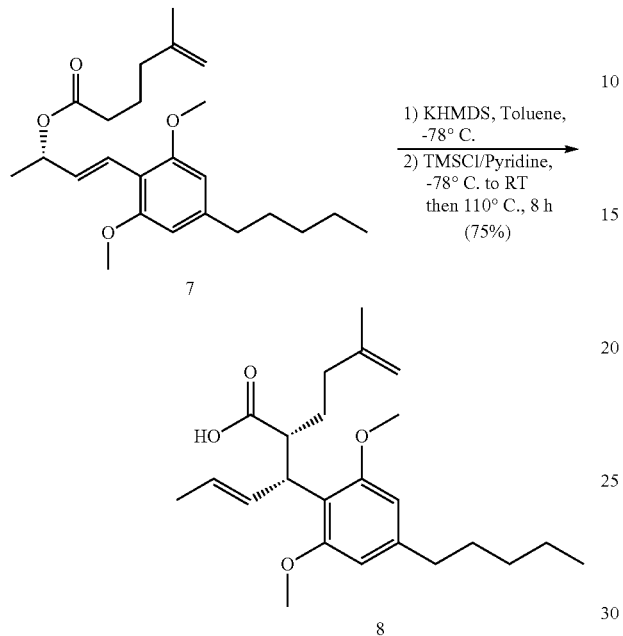

An esterification of compound 8 followed by a ring closing metathesis (RCM) of the enantioenriched methyl ester (8-Me) provides a cyclohexene intermediate 9, as shown in Scheme 5. The RCM process may be meditated, for example, by Grubb's 2nd generation catalyst. Advantageously, the RCM process disclosed herein produces the desired stereochemistry for the cyclohexene intermediates which may be used as synthetic precursors for cannabinoids and analogs. In one embodiment, subsequent steps may be carried out on intermediate 9 leading to the production of (−)-THC. These steps may include, for example, a Grignard addition followed by methyl ether deprotection under reduced pressure, which may provide a tertiary alcohol along with bisphenol. Lewis acid mediated ring-closure may be carried out using $ZnBr_2$ in the presence of $MgSO_4$ as a desiccant. All these transformations may be conducted in a two-pot manner with one purification step, which yield (−)-Δ9-THC with high stereoselectivity, such as over 90% ee.

-continued

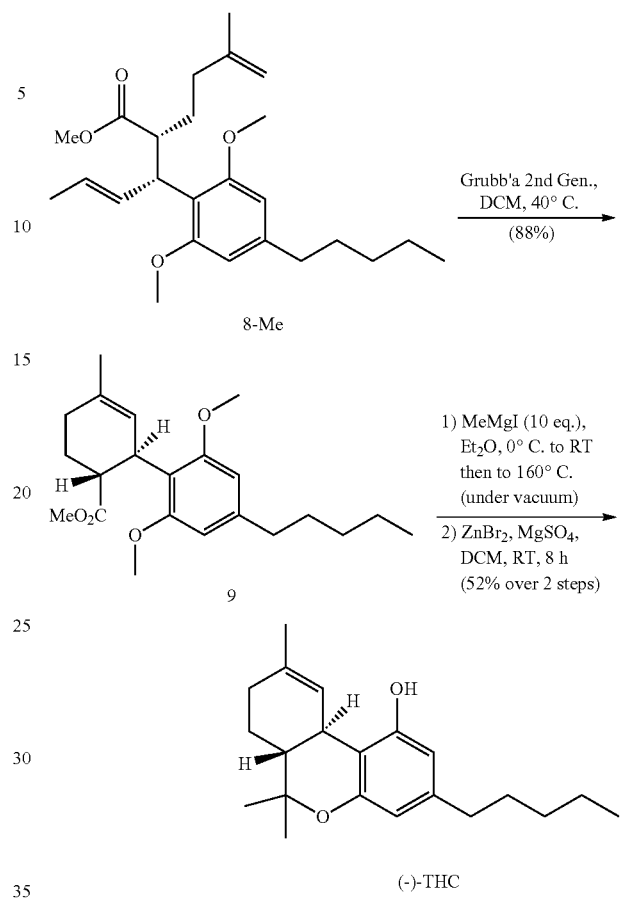

The Ireland-Claisen reaction product 8 may also be used as an intermediate for the production of CBD, as shown in Scheme 6. Interconversion from carboxylic acid 8 to ketone (8-CO), for example, with the use of methyl lithium may be achieved followed by a RCM to provide the cyclohexene intermediate 10 with the desired olefin geometry. Wittig olefination of the ketone may be carried out to provide intermediate 11 with the isopropenyl group found in CBD. Deprotection of the hydroxyl groups in 11 (for example, with NaSEt or MeMgI) provides the natural enantiomer of CBD.

Scheme 5

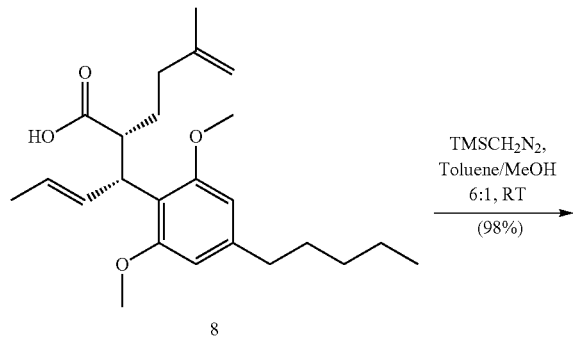

Scheme 6

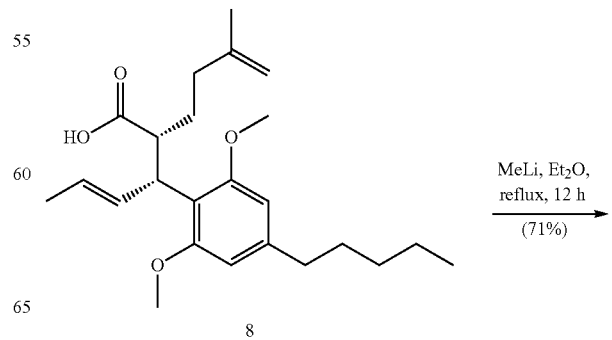

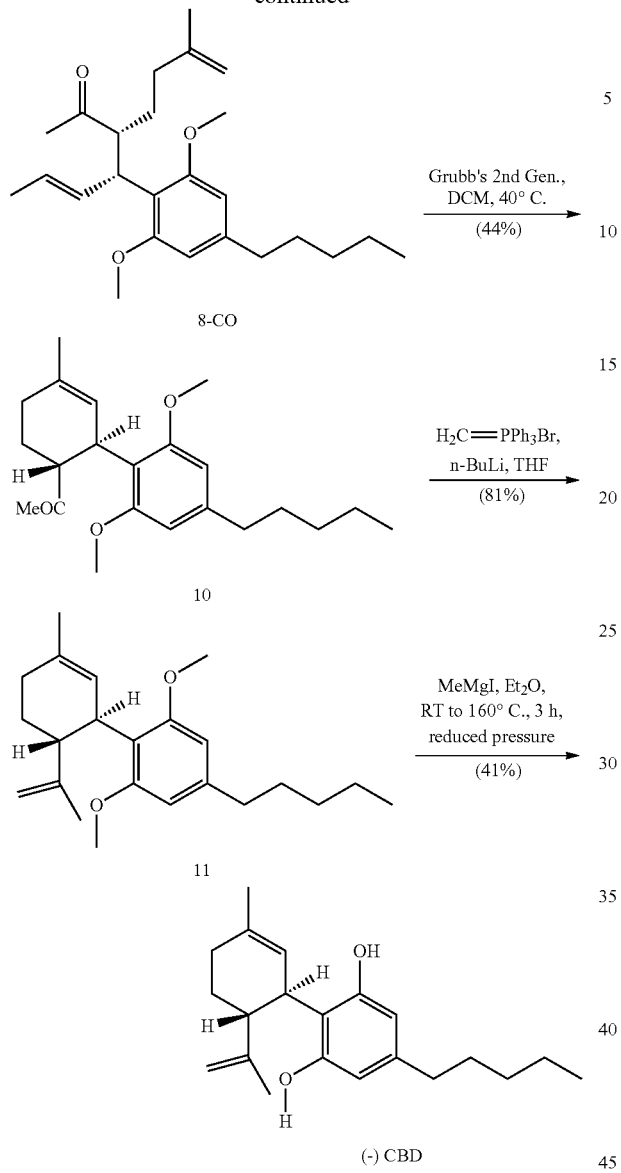

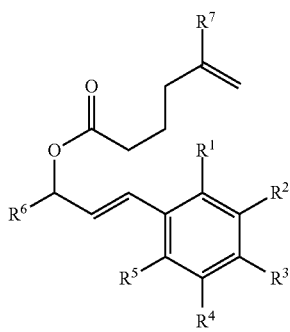

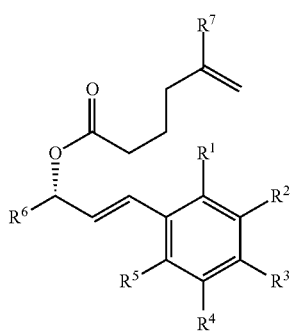

Disclosed herein is a new synthetic route towards the cannabinoids and their unnatural analogs. In certain embodiments, a controlled stereocenter (for example, one resulting from CBS reduction), can be used to transfer chirality to the α and β centers of the carboxylic acid intermediate 8. In certain embodiments, an Ireland-Claisen rearrangement may be used in a ring closure step to provide a single diastereomer of the cyclohexene intermediates (such as 9 and 10) with high stereoselectivity (for example, over 90% ee). The enantiomerically enhanced intermediates can be interconverted into THC or CBD in subsequent steps with desired stereochemistry.

All reactions conditions, reagents and % yields described above are non-limiting, representative depictions of the synthetic process disclosed herein. Variations of the above-described synthesis processes and intermediates, including for example variations in the alkyl side chains and conditions of certain transformations (such as the Grignard and/or Wittig reactions), are all contemplated by the instant invention.

3. Compound

In one aspect, disclosed is compound of formula (II), a racemate or a stereoisomer thereof.

wherein $R^1$ and $R^5$ are independently hydroxyl or a protected hydroxyl group;

$R^2$ and $R^4$ are independently hydrogen or $C_1$-$C_{10}$ alkyl;

$R^3$ is $C_1$-$C_{10}$ alkyl; and $R^6$ and $R^7$ are independently hydrogen or $C_1$-$C_{10}$ alkyl;

wherein $R^2$, $R^3$, $R^4$, $R^6$, and $R^7$ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle.

In certain embodiments, $R^1$ and $R^5$ are independently hydroxyl or $C_1$-$C_4$ alkoxy, such as —$OCH_3$.

In certain embodiments, $R^2$ and $R^4$ are independently hydrogen or $C_1$-C4 alkyl. In certain embodiments, $R^2$ and $R^4$ are hydrogen.

In certain embodiments, $R^3$ is $C_1$-$C_{10}$ alkyl, such as —$(CH_2)_2$—$CH_3$ or —$(CH_2)_4$—$CH_3$.

In certain embodiments, $R^6$ and $R^7$ are independently hydrogen or $C_1$-C4 alkyl. In certain embodiments, $R^6$ and $R^7$ are —$CH_3$.

In certain embodiments, the compound of formula (II), has a structure of formula (II-a).

In certain embodiments, the compound of formula (II) is (S,E)-4-(2,6-dimethoxy-4-pentylphenyl)but-3-en-2-yl 5-methylhex-5-enoate, having a structure of

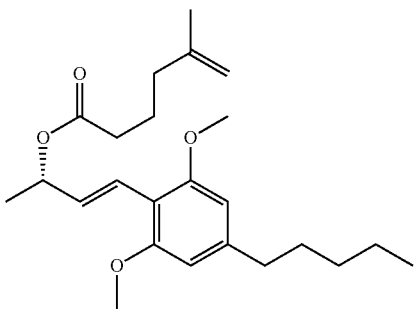 [SMILES: C=C(C)CCCC(=O)O[C@@H](C)/C=C/c1c(OC)cc(CCCCC)cc1OC]

In one aspect, disclosed is compound of formula (III), a racemate or a stereoisomer thereof.

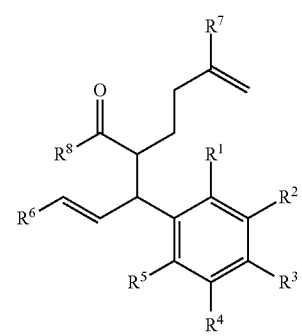

wherein

R¹ and R⁵ are independently hydroxyl or a protected hydroxyl group;

R² and R⁴ are independently hydrogen or $C_1$-$C_{10}$ alkyl;

R³ is $C_1$-$C_{10}$ alkyl;

R⁶ and R⁷ are independently hydrogen or $C_1$-$C_{10}$ alkyl; and

R⁸ is hydroxyl, $C_1$-$C_{10}$ alkyl, or $C_1$-$C_{10}$ alkoxy;

wherein R², R³, R⁴, R⁶, R⁷, and R⁸ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle.

In certain embodiments, R¹ and R⁵ are independently hydroxyl or $C_1$-$C_4$ alkoxy, such as —OCH₃.

In certain embodiments, R² and R⁴ are independently hydrogen or $C_1$-C4 alkyl. In certain embodiments, R² and R⁴ are hydrogen.

In certain embodiments, R³ is $C_1$-$C_{10}$ alkyl, such as —(CH₂)₂—CH₃ or —(CH₂)₄—CH₃.

In certain embodiments, R⁶ and R⁷ are independently hydrogen or $C_1$-C4 alkyl. In certain embodiments, R⁶ and R⁷ are —CH₃.

In certain embodiments, R⁸ is hydroxyl, $C_1$-$C_4$ alkyl such as —CH₃, or $C_1$-$C_4$ alkoxy such as —OCH₃.

In certain embodiments, the compound of formula (III), has a structure of formula (III-a).

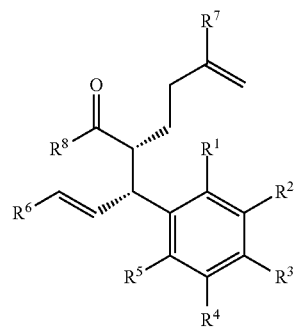

In certain embodiments, the compound of formula (III) is (2R,3R,E)-3-(2,6-dimethoxy-4-pentylphenyl)-2-(3-methylbut-3-en-1-yl)hex-4-enoic acid, having a structure of

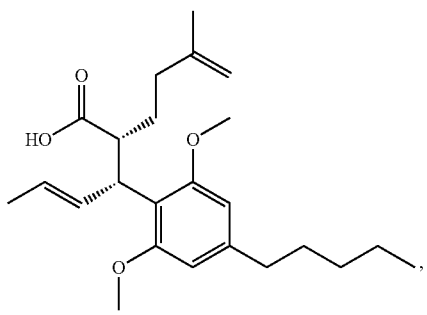 [SMILES: C=C(C)CC[C@@H](C(=O)O)[C@@H](/C=C/C)c1c(OC)cc(CCCCC)cc1OC]

methyl (2R,3R,E)-3-(2,6-dimethoxy-4-pentylphenyl)-2-(3-methylbut-3-en-1-yl)hex-4-enoate, having a structure of

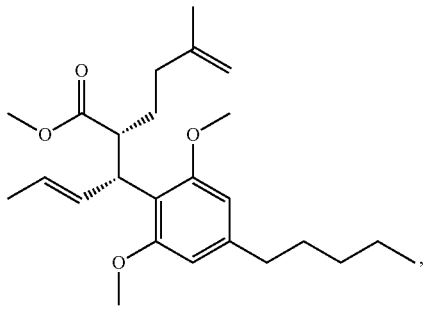 [SMILES: C=C(C)CC[C@@H](C(=O)OC)[C@@H](/C=C/C)c1c(OC)cc(CCCCC)cc1OC]

or (3R,4R,E)-4-(2,6-dimethoxy-4-pentylphenyl)-3-(3-methylbut-3-en-1-yl)hept-5-en-2-one, having a structure of

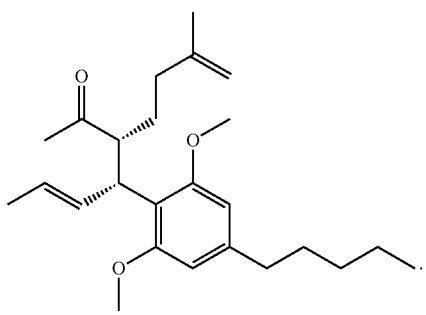 [SMILES: C=C(C)CC[C@@H](C(C)=O)[C@@H](/C=C/C)c1c(OC)cc(CCCCC)cc1OC]

Compounds of formula (II) and compounds of formula (III) are useful for preparing cannabinoids and their non-naturally occurring analogs according the processes disclosed herein. In some embodiments, a compound of formula (III) may be converted to a corresponding cannabinoid or analog thereof in one or more reactions as disclosed herein. In some embodiments, a compound of formula (II) may be converted to a corresponding compound of formula (III), which then may be converted to a corresponding cannabinoid or analog thereof in a one or more reactions as disclosed herein.

4. Examples

THC and CBD were synthesized in an approach starting with commercially available olivetol (1), as shown in Scheme 7. The phenols were protected as methyl ethers and formylation gave benzaldehyde 3 in excellent yields. An aldol reaction with acetone therefore provided enone 4 in high yield, and in an easily scalable reaction. The initial chirality (from which all of the stereocenters in the cannabinoids were set) was installed via the CBS mediated reduction of this ketone, which proceeded in good yield and in reproducible enantiomeric excesses of 70-80%. A scalable, enzymatic approach to generate products with high enantiopurity was also used herein, which involves reduction of compound 4 with sodium borohydride to provide the requisite racemic alcohol, followed by acylation with vinyl buyrate in the presence of Savinase 12T (resulting in ester with >98% ee). The enantiopurity of these compounds could be dramatically improved to >99% through the recrystallization of a subsequent intermediate (8), but in a practical sense, it was found that an enzymatic esterification of 5 using inexpensive and readily available sources such as subtilisin could be used to enhance these purities as well. Acylation of 5 with the known carboxylic acid 6 set the stage for an Ireland-Claisen rearrangement, which allowed translation of the alcohol stereochemistry into the 2 stereocenters of 8 with complete control. Intermediate 8 proved to be a branching point from which either THC or CBD could be prepared. The former was synthesized via the esterification of this crystalline carboxylic acid followed by olefin methathesis to form cyclohexene 9, then Grignard addition and zinc mediated demethylation and cyclization afforded THC. Alternatively, the acid could be converted into the methyl ketone prior to the ring closing methathesis to give 10. Wittig installation of the olefin followed by deprotection gave CBD.

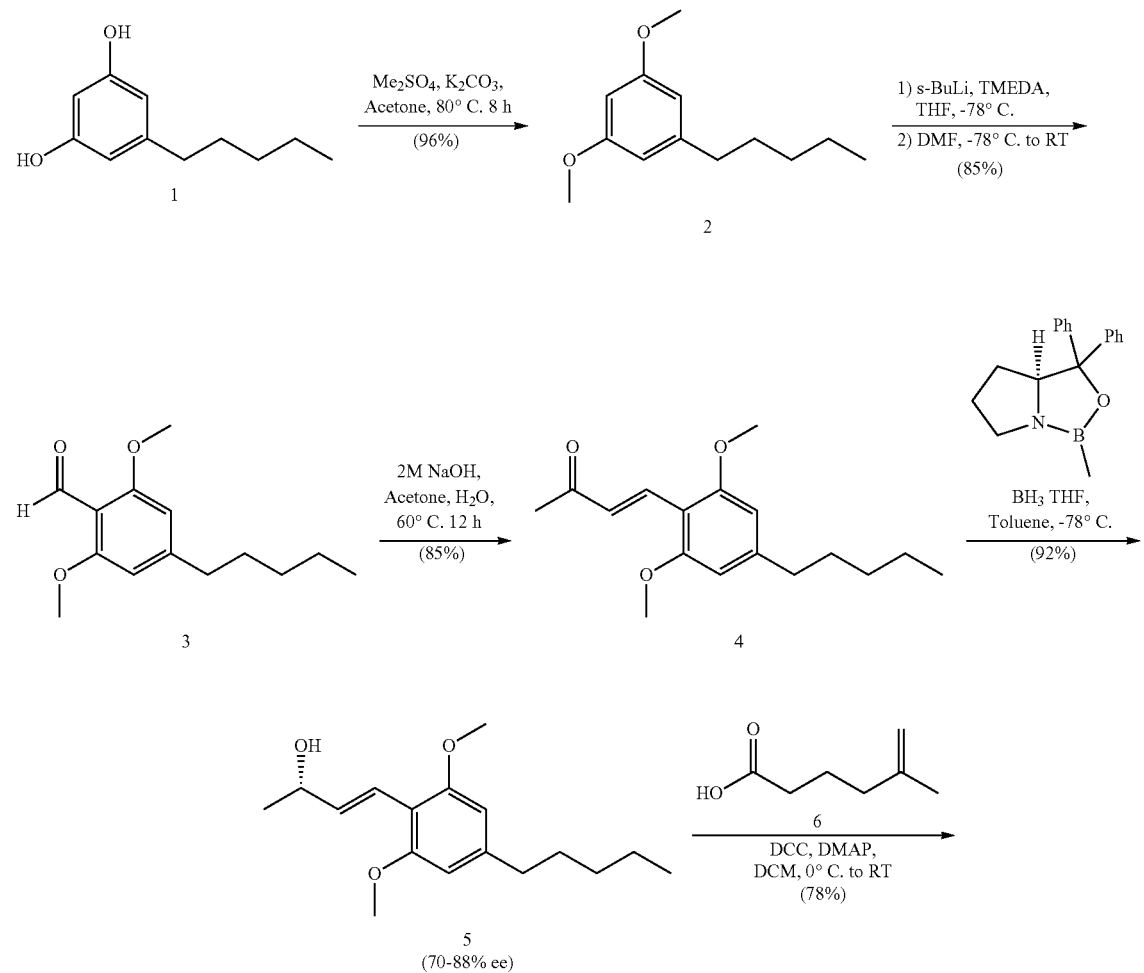

Scheme 7

-continued

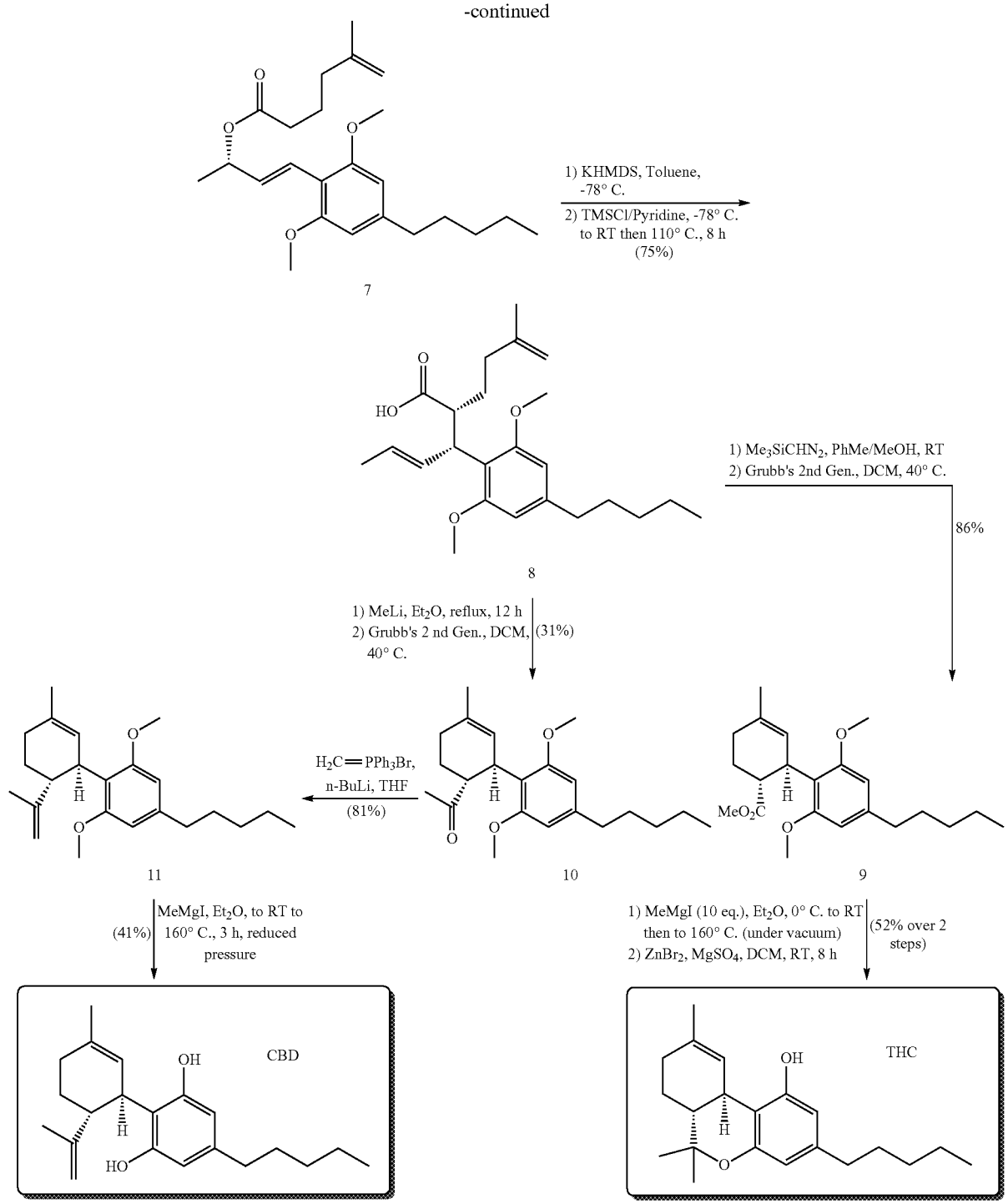

General Procedures

Unless otherwise noted, all materials were obtained from commercial suppliers and used without further purification. All reactions with air- and/or moisture-sensitive compounds were performed under an argon atmosphere in a flame-dried or oven-dried reaction flask, and reagents were added via syringe or cannula. Dry THF was obtained via distillation from sodium benzophenone ketyl. Microwave reactions were carried out with an Anton Paar Monowave 300 instrument. Preparative chromatography was carried out using Sorbtech silica gel (60 Å porosity, 40-63 μm particle size) in fritted MPLC cartridges and eluted with Thomson Instrument SINGLE StEP pumps. Thin layer chromatography analyses were conducted with 200 μm precoated Sorbtech fluorescent TLC plates. Plates were visualized by UV light and by staining with a variety of stains such as acidic anisaldehyde, acidic vanillin, ceric ammonium nitrate or iodine vapor. LC/MS data was obtained using an Agilent 1100 HPLC/MSD system equipped with a diode array detector running an acetonitrile/water gradient. High resolution mass spectral data were obtained using an Agilent 6540 QTOF mass spectrometer. Nuclear magnetic resonance spectrometry was run on a Varian Inova 500 MHz or a Varian Inova 400 MHz spectrometer, and chemical shifts are listed in ppm correlated to the solvent used as an internal standard. Optical rotations were performed on a Rudolph Research Analytical Autopol IV polarimeter (λ589) using a 700-μL cell with a path length of 1-dm. Enantiomeric excess (ee) was determined using a Varian Prostar HPLC with a 210 binary pump and a 335 diode array detector. IR spectra were obtained using Agilent Cary 630 FTIR.

Example 1. Compound 2

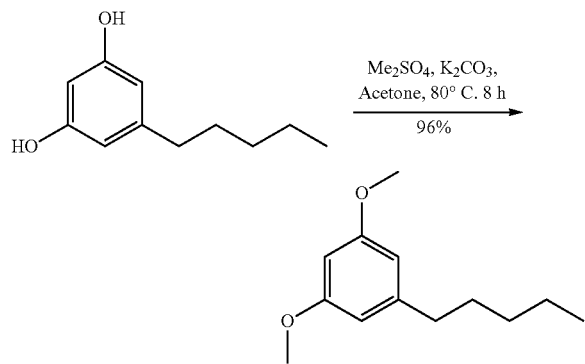

In a 500 mL round bottom flask equipped with a stir bar was added olivetol (10 g, 56 mmol) and $K_2CO_3$ (23 g, 0.17 mol) in 150 mL of acetone. $Me_2SO_4$ (15.9 mL, 166 mmol) was added dropwise for 5 minutes at room temperature then heated to 80° C. for 12 hours under argon, at which time olivetol was fully consumed (TLC). The reaction mixture was vacuum filtered and rinsed with $Et_2O$ (250 mL). The filtrate was washed with 1N HCl (175 mL), brine (100 mL×2), dried over MgSO4, filtered and concentrated to give an orange oil. The crude oil was purified by silica gel column chromatography using Hexanes/EtOAc (9:1) to give compound 2 (11.3 g, 54.2 mmol, 98% yield) as a yellow orange oil. $^1$H NMR (400 MHz, CDCl$_3$) δ 6.35 (d, J=2.3 Hz, 2H), 6.30 (t, J=2.3 Hz, 1H), 3.78 (s, 6H), 2.55 (t, J=7.4 Hz, 2H), 1.57-1.66 (m, 2H), 1.28-1.38 (m, 4H), 0.90 ppm (t, J=6.6 Hz, 3H) ppm. $^{13}$C NMR (101 MHz, CDCl$_3$) δ160.7, 145.4, 106.4, 97.5, 55.2, 36.3, 31.5, 31.0, 22.5, 14.0 ppm. HRMS m/z: [M+H]$^-$ calculated for $C_{13}H_{21}O_2$ 209.1536, found 209.1527.

Example 2. Compound 3

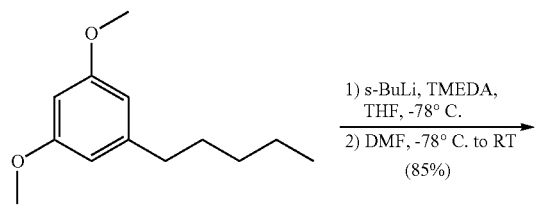

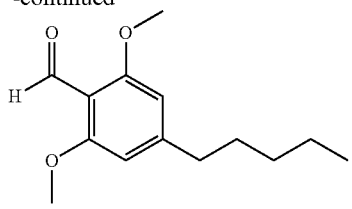

In a flame dried 500 ml double neck flask equipped with a stir bar was 1,3-dimethoxy-5-pentylbenzene (10 g, 48.0 mmol) and TMEDA (8.69 ml, 57.6 mmol) in 192 ml of anhydrous THF at −78° C. to give a yellow solution. Once cool, sec-butyllithium (41.2 ml, 1.4 M in hexanes, 57.6 mmol) was added dropwise over 10 minutes and the reaction continued to stir at −78° C. for 30 minutes before warming to 0° C. as the mixture continued to stir for an additional 60 minutes. At this time anhydrous DMF (4.46 ml, 57.6 mmol) in 10 ml of anhydrous THF was added to the reaction mixture dropwise over 2 minutes. The reaction continued to stir at 0° C. for 30 minutes before warming to room temperature. Once at room temperature the reaction stirred for an additional 60 minutes before quenching with sat. aq. $NH_4Cl$ (75 ml) and DI water (25 ml). The aqueous layer was extracted with EtOAc (3×75 ml) and combined organic layers were washed with brine (75 ml), dried over $Na_2SO_4$, filtered and concentrated to give a yellow oil. The crude oil was purified by column chromatography using Hexanes/EtOAc (4:1) to give 2,6-dimethoxy-4-pentylbenzaldehyde (9.6 g, 40.5 mmol, 85% yield) of a yellow oil. $^1$H NMR (400 MHz, CDCl$_3$) δ 10.42 (s, 1H), 6.36 (s, 2H), 3.86 (s, 6H), 2.57 (t, J=7.4 Hz, 2H), 1.58-1.65 (m, 2H), 1.29-1.35 (m, 4H), 0.88 (t, J=6.6 Hz, 3H) ppm. $^{13}$C NMR (126 MHz, CDCl$_3$) δ 188.9, 162.2, 152.5, 112.2, 103.9, 55.9, 37.2, 31.5, 30.5, 22.5, 14.0 ppm. HRMS m/z: [M+H]$^+$ calculated for $C_{14}H_{21}O_3$ 237.1485, found 237.1483.

Example 3. Compound 4

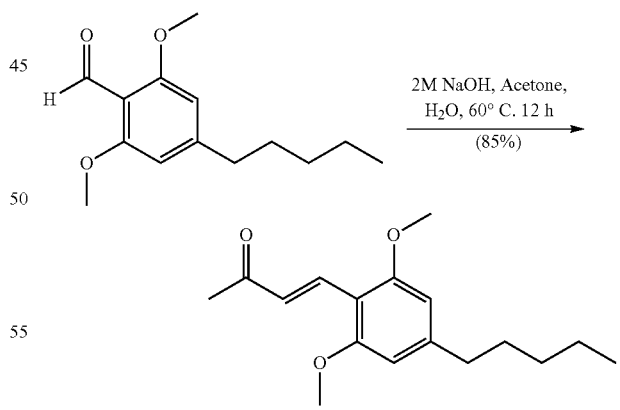

In a 500 ml round bottom flask equipped with a stir bar was 2,6-dimethoxy-4-pentylbenzaldehyde (9.62 g, 40.6 mmol) in 203 ml of water. A solution of acetone (14.9 ml, 203 mmol) and 2.5M NaOH (55.3 ml, 138 mmol) were added quickly and the reaction mixture which was heated to 60° C. for 12 hours. At this time the reaction was complete (TLC, Hex/EtOAc, 4:1, CAM). The reaction mixture was cooled to room temperature and diluted with $Et_2O$ (100 ml)

and the aqueous layer was extracted with Et$_2$O (3×150 ml). The combined organic layers were washed with 1N HCl (150 ml), brine (75 ml), dried over Na$_2$SO$_4$, filtered and concentrated to give an orange oil. The crude oil was purified by column chromatography using Hexanes/EtOAc (5:1) to give a yellow oil that solidified into a light yellow crystalline solid (10.1 g, 362 mmol, 89% yield). $^1$H NMR (400 MHz, CDCl$_3$) δ 7.96 (d, J=16.8 Hz, 1H), 7.12 (d, J=16.4 Hz, 1H), 6.38 (s, 2H), 3.87 (s, 6H), 2.58 (t, J=7.6 Hz, 2H), 2.35 (s, 3H), 1.57-1.68 (m, 2H), 1.34 (d, J=3.1 Hz, 4H), 0.90 (t, J=6.4 Hz, 3H) ppm. $^{13}$C NMR (126 MHz, CDCl$_3$) δ200.6, 160.0, 147.7, 135.1, 129.3, 109.7, 103.9, 55.7, 36.9, 31.5, 30.8, 26.9, 22.5, 14.0 ppm. HRMS m/z: [M+H]$^+$ calculated for C$_{17}$H$_{25}$O$_3$ 277.1804; found 277.1797.

Example 4. Compound 5

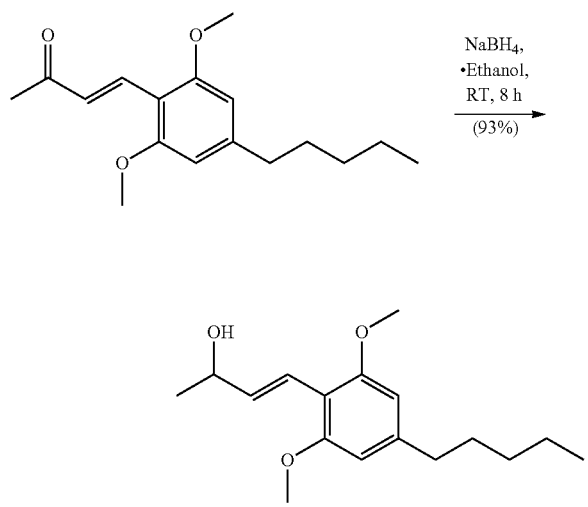

In a 100 round bottom flask equipped with a stir bar was (E)-4-(2,6-dimethoxy-4-pentylphenyl)but-3-en-2-one (4.15 g, 15.1 mmol) in 65.3 ml of EtOH and the solution was cooled to 0° C. Once cool, NaBH$_4$ (0.625 g, 16.5 mmol) was added and the reaction mixture stirred at 0° C. for 2.5 hours before warming to room temperature for 18 hours at which time the reaction was complete (TLC, 4:1 Hex/EtOAc). The solvent was removed under vacuum and the crude oil was dissolved in 100 ml of EtOAc and 75 ml of water. The aqueous layer was extracted with EtOAc (3×150 ml), organic layers were washed with brine (120 ml), dried over Na$_2$SO$_4$, filtered and concentrated to give 4.2 g of an opaque oil that was purified by silica gel column chromatography using Hexanes/EtOAc (3:1) to give (3.9 g, 14 mmol, 93% yield) a clear colorless oil that solidifies upon standing. IR (neat): 3424, 2959, 2933, 2858, 1610, 1577, 1458, 1420, 1119, 1052, 981, 828 cm$^{-1}$. $^1$H NMR (400 MHz, CDCl$_3$) δ 6.81 (d, J=16.1 Hz, 1H), 6.62 (dd, J=16.2, 7.0 Hz, 4H), 6.36 (s, 2H), 4.34-4.49 (m, 1H), 3.82 (s, 6H), 2.55 (t, J=7.4 Hz, 2H), 1.56-1.62 (m, 3H), 1.34 (d, J=6.2 Hz, 3H), 1.27-1.33 (m, 4H), 0.88 (t, J=7.0 Hz, 3H) ppm. $^{13}$C NMR (126 MHz, CDCl$_3$) δ 158.3, 143.7, 136.5, 120.1, 111.2, 104.1, 70.8, 55.6, 36.6, 31.5, 31.0, 23.4, 22.5, 14.0 ppm. HRMS m/z: [M+Na]$^+$ calculated for C$_{17}$H$_{26}$O$_3$Na 301.1774, found 301.1765.

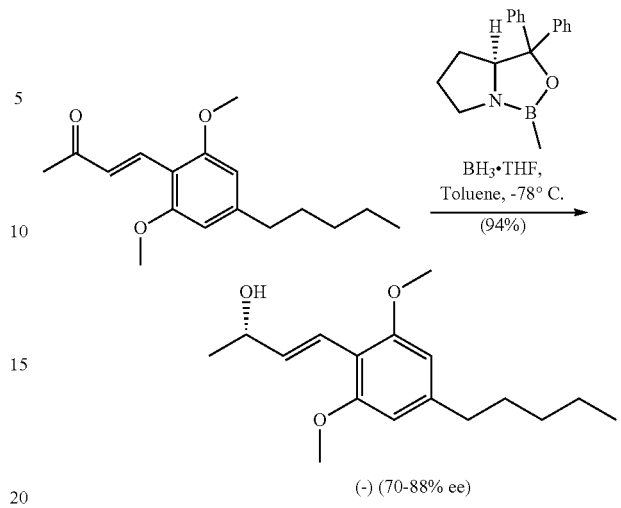

In a 250 ml double-necked round bottom flask equipped with a stir bar was (E)-4-(2,6-dimethoxy-4-pentylphenyl)but-3-en-2-one (2.0 g, 7.2 mmol) in Toluene (145 ml) at −78° C. under argon. Once cool, a solution of (R)-CBS ligand (7.96 ml, 7.96 mmol, 1M in Toluene) was added dropwise over 5 minutes then stirred for an additional 10 minutes. A solution of BH$_3$·THF complex (7.96 ml, 7.96 mmol, 1M in THF) was added dropwise over 5 minutes and the reaction mixture continued to stir for 30 minutes. At this time the ketone was fully consumed (TLC Hex/EtOAc, 4:1) and the reaction mixture was carefully quenched with cold 1M NaOH (50 ml). The aqueous bilayer was extracted with EtOAc (3×50 ml), washed with saturated aq. NaHCO$_3$ (50 ml), brine (50 ml). The organic layer was dried over Na$_2$SO$_4$ and filtered to give an oily suspension. The crude could be further purified by column chromatography using a gradient of Hex/EtOAc (4:1 to 2:1) to give (1.9 g, 6.8 mmol, 94% yield, ee 77%) of a clear colorless oil that solidified upon standing. HPLC Analysis: Chiralcel AD-H (Hexane:Isopropanol 85:15, 1.0 mL/min), t r-major 5.82 min, t r-minor 6.61 min. [α]$^{20}_D$=−13 (c=0.1, CHCl$_3$). IR (neat): 3424, 2959, 2933, 2858, 1610, 1577, 1458, 1420, 1119, 1052, 981, 828 cm$^{-1}$. $^1$H NMR (400 MHz, CDCl$_3$) δ 6.81 (d, J=16.1 Hz, 1H), 6.62 (dd, J=16.2, 7.0 Hz, 4H), 6.36 (s, 2H), 4.34-4.49 (m, 1H), 3.82 (s, 6H), 2.55 (t, J=7.4 Hz, 2H), 1.56-1.62 (m, 3H), 1.34 (d, J=6.2 Hz, 3H), 1.27-1.33 (m, 4H), 0.88 (t, J=7.0 Hz, 3H) ppm. $^{13}$C NMR (126 MHz, CDCl$_3$) δ 158.3, 143.7, 136.5, 120.1, 111.2, 104.1, 70.8, 55.6, 36.6, 31.5, 31.0, 23.4, 22.5, 14.0 ppm. HRMS m/z: [M+Na]$^+$ calculated for C$_{17}$H$_{26}$O$_3$Na 301.1774, found 301.1765.

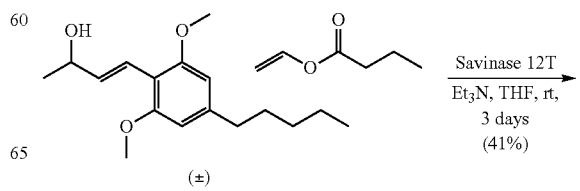

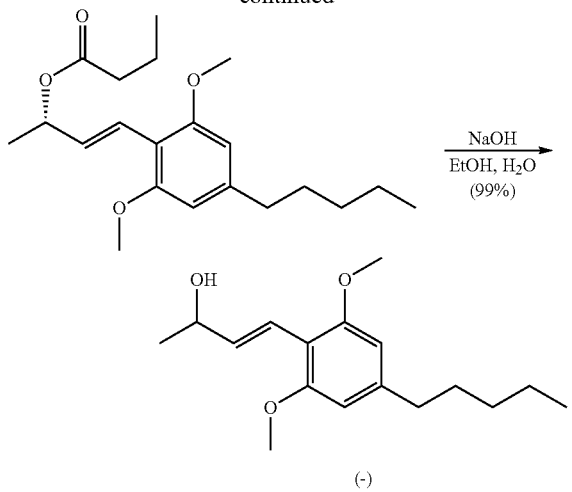

In a 50 mL round-bottomed flask equipped with a stir bar was added Savinase 12T (2.38 g, 100% w/w) in anhydrous THF (17.1 mL) to give a white suspension. Et$_3$N (1.19 mL, 8.55 mmol), vinyl butyrate (3.25 mL, 25.6 mmol) and (E)-4-(2,6-dimethoxy-4-pentylphenyl)but-3-en-2-ol (2.38 g, 8.55 mmol) were added and the reaction vessel was purged with argon. The reaction continued to stir at rt for 3 days while reaction progress was monitored by chiral HPLC. At this time the reaction mixture was vacuum S9 filtered through a pad of Celite while rinsing with EtOAc. The solvents were removed under reduced pressure to give a light yellow oil that was purified by silica gel column chromatography using hexanes/EtOAc (10:1) with 2% Et$_3$N to give 13.1 (1.22 g, 3.51 mmol, 41% yield) as a clear light yellow oil. Compound (S,E)-4-(2,6-dimethoxy-4-pentylphenyl)but-3-en-2-yl butyrate was dissolved in a 5% NaOH solution of ethanol and water (5:1, 43 mL) and heated to reflux for 3 h. At this time the ester was no longer visible by TLC and the reaction was cooled to rt. Ethanol was removed under reduced pressure and the residue was diluted with water (20 mL) and DCM (50 mL). The aqueous layer was extracted with DCM (3×50 mL) and the combined organic layers were dried over Na$_2$SO$_4$, filtered and concentrated to give (S,E)-4-(2,6-dimethoxy-4-pentylphenyl)but-3-en-2-ol (1.21 g, 3.50 mmol, 99% yield, ee>98%) as a light yellow oil without further purification. HPLC Analysis: Chiralcel AD-H (Hexane:Isopropanol 85:15, 1.0 mL/min), t r-major 5.82 min, t r-minor 6.61 min.

Example 5. Compound 7

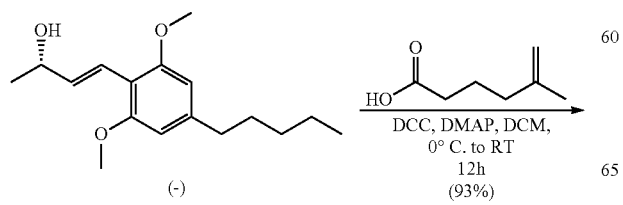

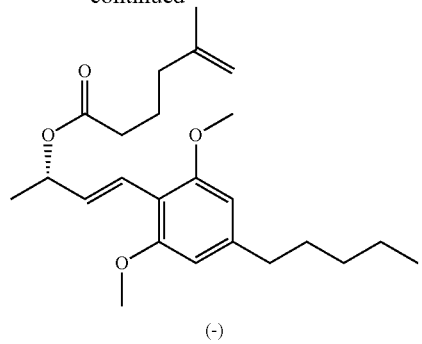

In a 100 ml round bottom flask equipped with a stir bar was (S,E)-4-(2,6-dimethoxy-4-pentylphenyl)but-3-en-ol (1.32 g, 4.67 mmol) in DCM at 0° C. DCC (1.34 g, 6.54 mmol) and DMAP (0.057 g, 0.467 mmol) were added to the cold stirring solution. 5-methylhex-5-enoic acid (0.838 ml, 4.67 mmol) was then added and the reaction stirred at 0° C. for 1 hour before warming to room temperature where it stirred overnight. Once the reaction was complete (TLC, Hex/EtOAc, 9:1) the solid was filtered and rinsed with DCM (25 ml). The resulting filtrate was washed with 1N HCl (25 ml), sat. aq. NaHCO$_3$ (25 ml), brine (25 ml), filtered and concentrated to give an oily solid. The crude material was purified by column chromatography using Hex/EtOAc (20:1 to 10:1) and 2% Et$_3$N to give (S,E)-4-(2,6-dimethoxy-4-pentylphenyl)but-3-en-2-yl 5-methylhex-5-enoate (1.68 g, 4.32 mmol, 93% yield, >98% ee) as a clear colorless oil. HPLC Analysis: Chiralcel AD-H (Hexane:Isopropanol 98:2, 1.0 mL/min), t r-major 5.63, t r-minor 5.13 min. [α]$^{20}_D$=−59 (c=0.1, CHCl$_3$). IR (neat): 2933, 2862, 1733, 1610, 1577, 1458, 1420, 1238, 1204, 1160, 1119, 1096, 1041, 981, 892, 828 cm$^{-1}$. $^1$H NMR (400 MHz, CDCl$_3$) δ 6.89 (d, J=16.0 Hz, 1H), 6.54-6.62 (m, 1H), 6.35 (s, 2H), 5.51 (app. quin, J=6.6 Hz, 1H), 4.71 (s, 1H), 4.66-4.69 (m, 1H), 3.82 (s, 6H), 2.54 (t, J=7.8 Hz, 2H), 2.30 (t, J=7.4 Hz, 2H), 2.04 (t, J=7.4 Hz, 2H), 1.78 (app. quin, J=7.6 Hz, 2H), 1.70 (s, 3H), 1.56-1.64 (m, 2H), 1.38 (d, J=6.6 Hz, 3H), 1.27-1.34 (m, 4H), 0.88 (t, J=6.4 Hz, 3H) ppm. $^{13}$C NMR (101 MHz, CDCl$_3$) δ 172.9, 158.4, 144.9, 143.9, 131.4, 122.1, 110.9, 110.5, 104.1, 72.9, 55.6, 37.1, 36.6, 34.2, 31.5, 31.0, 22.9, 22.5, 22.2, 20.7, 14.0 ppm. HRMS m/z: [M+Na]$^+$ calculated for C$_{24}$H$_{36}$O$_4$Na 411.2506, found 411.2498.

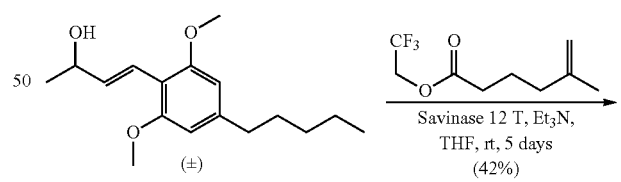

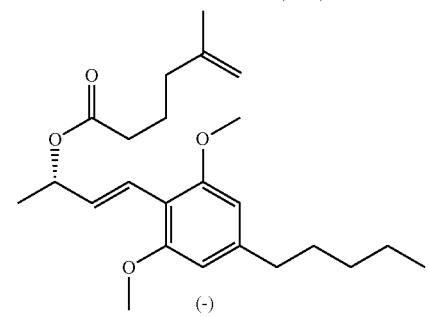

In a 50 mL round-bottomed flask equipped with a stir bar was added Savinase 12T (1 g, 50% w/w) in THF (14.4 mL). 2,2,2-Trifluoroethyl 5-methylhex-5-enoate (vide infra, 2.26 g, 10.7 mmol), (E)-4-(2,6-dimethoxy-4-pentylphenyl)but-3-en-2-ol (2.0 g, 7.2 mmol) and Et3N (1.1 mL, 7.2 mmol) were added to the vigorously stirred solution. The reaction vessel was purged with argon and stirred at rt for 5 days. At this time the reaction was deemed complete (chiral HPLC analysis) and vacuum filtered through a pad of Celite while rinsing with EtOAc. The filtrate was concentrated under reduced pressure and purified by silica gel column chromatography using hexanes:EtOAc (15:1) and 2% Et$_3$N to give (S,E)-4-(2,6-dimethoxy-4-pentylphenyl)but-3-en-2-yl 5-methylhex-5-enoate (1.18 g, 3.03 mmol, 42% yield, 99% ee) as a clear light yellow oil. HPLC Analysis: Chiralcel AD-H (Hexane:Isopropanol 98:2, 1.0 mL/min), t r-major 5.63, t r-minor 5.13 min. $[\alpha]^{20}{}_D$=−59 (c=0.1, CHCl3). $^1$H NMR (400 MHz, CDCl3): δ 6.89 (d, J=16.0 Hz, 1H), 6.54-6.62 (m, 1H), 6.35 (s, 2H), 5.51 (app. quin, J=6.6 Hz, 1H), 4.71 (s, 1H), 4.66-4.69 (m, 1H), 3.82 (s, 6H), 2.54 (t, J=7.8 Hz, 2H), 2.30 (t, J=7.4 Hz, 2H), 2.04 (t, J=7.4 Hz, 2H), 1.78 (app. quin, J=7.6 Hz, 2H), 1.70 (s, 3H), 1.56-1.64 (m, 2H), 1.38 (d, J=6.6 Hz, 3H), 1.27-1.34 (m, 4H), 0.88 ppm (t, J=6.4 Hz, 3H) ppm. $^{13}$C NMR (101 MHz, CDCl3) δ 172.9, 158.4, 144.9, 143.9, 131.4, 122.1, 110.9, 110.5, 104.1, 72.9, 55.6, 37.1, 36.6, 34.2, 31.5, 31.0, 22.9, 22.5, 22.2, 20.7, 14.0 ppm. HRMS m/z: [M+Na]$^+$ calculated for C$_{24}$H$_{36}$O$_4$Na 411.2506, found 411.2498.

Example 6. Compound 8

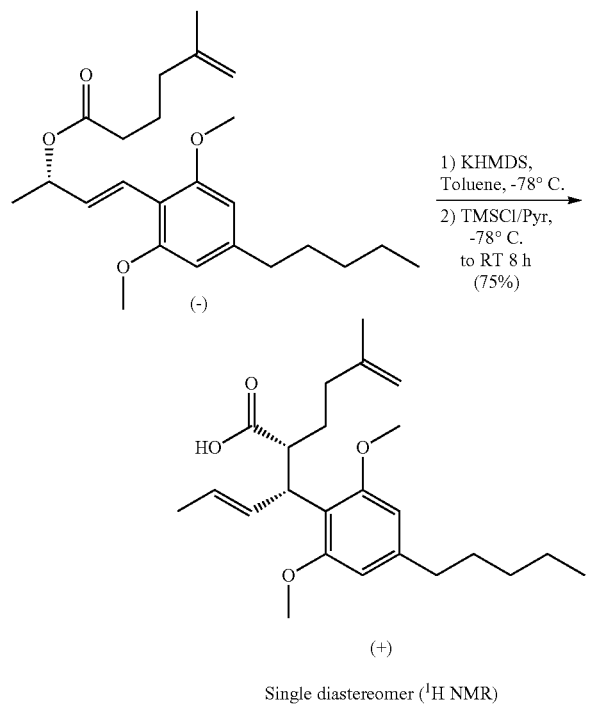

Single diastereomer ($^1$H NMR)

In a double necked 150 ml round bottom flask equipped with a stir bar was KHMDS (14.4 ml, 7.23 mmol, 0.5M in Toluene) in anhydrous toluene (19.2 ml) at −78° C. Once cooled a solution of (E)-4-(2,6-dimethoxy-4-pentylphenyl)but-3-en-2-yl-5-methylhex-5-enoate (0.932 g, 2.39 mmol) in anhydrous toluene (19.2 ml) was added via addition funnel over 10 minutes and stirred for 1 hour at −78° C. At this time a solution of anhydrous pyridine (0.871 ml, 10.7 mmol) and TMS-Cl (1.56 ml, 11.9 mmol) in anhydrous toluene (9.57 ml) was added via addition funnel over 5 minutes and continued to stir at −78° C. for 10 minutes before warming to room temperature where it stirred for an additional 4 hours. The reaction was quenched with saturated aqueous NH$_4$Cl (25 ml) followed by 1M HCl (20 ml) and stirred vigorously for 20 minutes. The layers were partitioned in a separatory funnel and extracted with EtOAc (3×50 ml), combined organic layers were washed with brine (50 ml), dried over Na$_2$SO$_4$, filtered and concentrated to give 1.5 g of an oily solid. The crude material was further purified by column chromatography using Hex/EtOAc (4:1) to give (2R,3R,E)-3-(2,6-dimethoxy-4-pentylphenyl)-2-(3-methyl-but-3-en-1-yl)hex-4-enoic acid (0.712 g, 1.87 mmol, 77% yield, 77% ee) of a white crystalline solid that could be recrystallized using hexanes to 94% ee. Starting material from kinetic enzymatic resolution with ee of 99% can be used to obtain the rearranged product with ee of 99%. HPLC Analysis: Chiralcel AD-H (Hexane:Isopropanol 95:5, 1.0 mL/min), t r-major 6.16 min, t r-minor 7.39. $[\alpha]^{20}{}_D$=+38 (c=0.1, CHCl3) at >98% ee. Melting point range: 113-115° C. IR (neat): 3300-2500 (br, COOH dimer), 3074, 3011, 2929, 2858, 2664, 1704, 1610, 1584, 1458, 1424, 1231, 1126, 974, 892, 821 cm$^{-1}$. $^1$H NMR (500 MHz, CDCl3) δ 6.32 (s, 2H), 5.77 (ddd, J=15.2, 9.3, 1.5 Hz, 1H), 5.54 (dq, J=15.2, 6.4 Hz, 1H), 4.71 (s, 1H), 4.68 (s, 1H), 4.04 (t, J=10.3 Hz, 1H), 3.77 (s, 6H), 3.18 (td, J=10.8, 3.4 Hz, 1H), 2.51 (t, J=7.8 Hz, 2H), 1.98-2.04 (m, 2H), 1.79-1.86 (m, 1H), 1.71 (s, 3H), 1.64-1.73 (m, 1H), 1.63 (dd, J=6.4, 1.5 Hz, 3H), 1.55-1.60 (m, 2H), 1.29-1.37 (m, 4H), 0.90 (t, J=6.8 Hz, 3H) ppm. $^{13}$C NMR (126 MHz, CDCl$_3$) δ 180.1, 157.9, 145.4, 142.7, 130.9, 127.0, 116.0, 110.1, 104.9, 55.8, 47.5, 42.0, 36.5, 35.7, 31.7, 31.0, 29.5, 22.6, 22.4, 17.9, 14.1 ppm. HRMS m/z: [M+H]$^+$ calculated for C$_{24}$H$_{37}$O$_4$ 389.2686, found 389.2676. The stereochemistry of this compound was established through the auspices of single crystal x-ray crystallography.

Example 7. Compound 9 (Step 1)

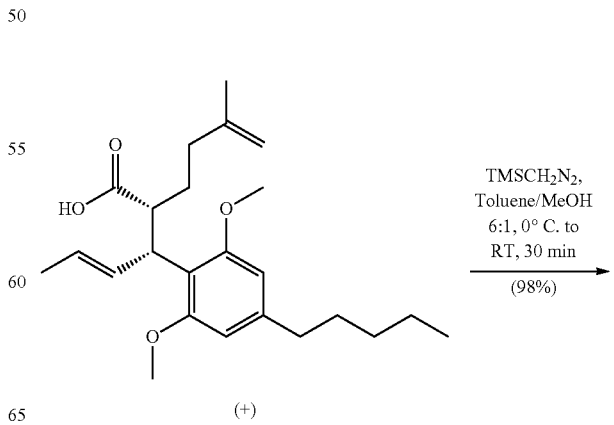

37

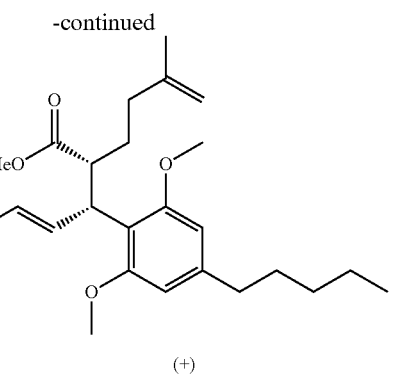

(+)

In a 25 ml round bottom flask equipped with a stir bar was (E)-3-(2,6-dimethoxy-4-pentylphenyl)-2-(3-methylbut-3-en-yl)hex-4-enoic acid (0.330 g, 0.849 mmol) in toluene/methanol (6:1, 42.5 mL) at 0° C. TMS-diazomethane (0.467 ml, 0.934 mmol) was added dropwise to the stirring solution. The evolution of $N_2$ was evident and the reaction mixture was allowed to warm to RT once $N_2$ evolution ceased. After 30 minutes the solvents were removed under reduced pressure and the crude material could be further purified by column chromatography using Hex/EtOAc 9:1 to give methyl (2R,3R,E)-3-(2,6-dimethoxy-4-pentylphenyl)-2-(3-methylbut-3-en-1-yl)hex-4-enoate (0.330 g, 0.820 mmol, 97% yield) as clear colorless oil. $[\alpha]^{20}_D$=+29 (c=0.1, CHCl$_3$). IR (neat): 2933, 2858, 1737, 1610, 1584, 1458, 1424, 1227, 1160, 1126, 974, 892, 825 cm$^{-1}$. $^1$H NMR (500 MHz, CDCl3): δ 6.32 (s, 2H), 5.80 (ddd, J=15.2, 9.5, 1.7 Hz, 1H), 5.55 (dq, J=15.1, 6.4 Hz, 1H), 4.70 (s, 1H), 4.68 (s, 1H), 4.03 (t, J=10.0 Hz, 1H), 3.79 (s, 6H), 3.27 (s, 3H), 3.16 (td, J=11.0, 3.4 Hz, 1H), 2.51 (t, J=7.3 Hz, 2H), 1.96 (t, J=7.8 Hz, 2H), 1.76-1.84 (m, 1H), 1.71 (s, 3H), 1.65-1.71 (m, 1H), 1.63 (dd, J=6.6, 1.7 Hz, 3H), 1.56-1.60 (m, 2H), 1.27-1.34 (m, 4H), 0.89 ppm (t, J=7.1 Hz, 3H) ppm. $^{13}$C NMR (126 MHz, CDCl$_3$): δ 176.0, 157.9, 145.6, 142.6, 131.1, 127.0, 116.3, 109.9, 104.8, 55.9, 50.7, 48.0, 42.4, 36.4, 35.9, 31.6, 31.0, 29.5, 22.5, 22.5, 17.9, 14.1 ppm. HRMS m/z: [M+Na]$^+$ calculated for C$_{25}$H$_{38}$O$_4$Na 425.2662; found 425.2660.

Example 8. Compound 9 (Step 2)

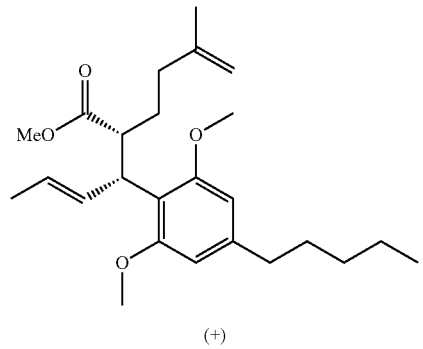

(+)

Grubb's 2nd Gen., 15% DCM, 40° C., 18h
(88%)
→

38

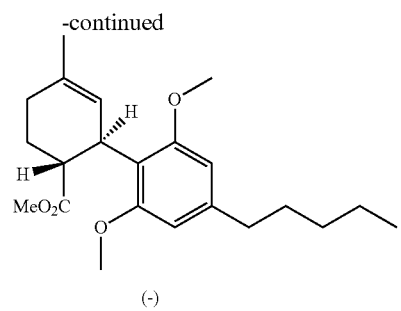

(-)

In a 100 ml round bottom flask equipped with a stir bar was (E)-methyl 3-(2,6-dimethoxy-4-pentylphenyl)-2-(3-methylbut-3-en-1-yl)hex-4-enoate (0.306 g, 0.745 mmol) in degassed DCM (37.3 ml, degassed with N2 flow for 15 min) under argon. Grubb's 2nd generation catalyst (0.048 g, 0.075 mmol) was added to the reaction mixture. The vessel was evacuated and purged with argon then heated to 40° C. for 12 hours. At this time a small amount of starting material was still present by TLC (Hex/EtOAc, 9:1). An additional 0.05 eq. of Grubb's 2nd generation catalyst (0.024 g, 0.038 mmol) was added to the reaction mixture and heated to 40° C. for 3 hours. The reaction was cooled to room temperature and the solvent was removed under reduced pressure to give a reddish oil. The crude oil was purified by column chromatography using Hex/EtOAc (9:1) to provide methyl (1R, 2R)-2',6'-dimethoxy-5-methyl-4'-pentyl-1,2,3,4-tetrahydro-[1,1'-biphenyl]-2-carboxylate (0.236 g, 0.655 mmol, 88% yield) as light yellow oil. $[\alpha]^{20}_D$=−137 (c=0.1, CHCl$_3$). $^1$H NMR (400 MHz, CDCl$_3$) δ 6.33 (s, 2H), 5.15 (s, 1H), 4.19-4.26 (m, 1H), 3.73 (s, 6H), 3.45 (s, 3H), 3.16 (ddd, J=12.6, 10.3, 2.9 Hz, 1H), 2.53 (t, J=7.8 Hz, 2H), 2.07-2.20 (m, 1H), 2.01 (d, J=13.7 Hz, 2H), 1.93-1.80 (m, 1H), 1.65 (s, 3H), 1.56-1.63 (m, 2H), 1.29-1.37 (m, 4H), 0.89 (t, J=7.0 Hz, 3H) ppm. $^{13}$C NMR (126 MHz, CDCl$_3$) δ 176.7, 158.6, 142.5, 130.9, 124.6, 117.4, 105.0, 56.0, 51.1, 43.4, 36.4, 34.8, 31.6, 31.0, 29.4, 27.1, 23.3, 22.6, 14.1 ppm. HRMS m/z: [M+Na]$^+$ calculated for C$_{22}$H$_{32}$O$_4$Na 383.2193; found 383.2193.

Example 9. Δ$^9$-tetrahydrocannabinol (THC)

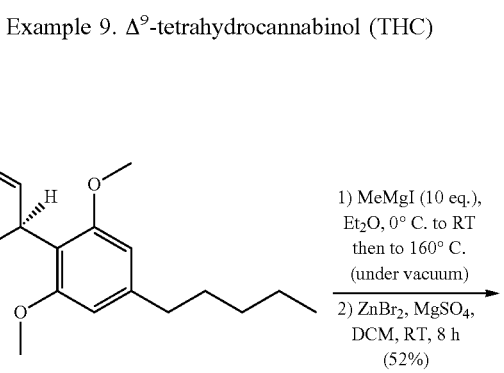

(-)

1) MeMgI (10 eq.), Et$_2$O, 0° C. to RT then to 160° C. (under vacuum)
2) ZnBr$_2$, MgSO$_4$, DCM, RT, 8 h
(52%)
→

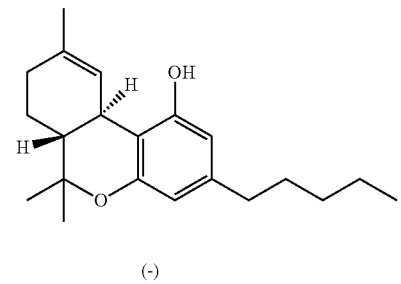

(-)

In a 25 ml round bottom flask equipped with a stir bar was methyl ester (0.022 g, 0.061 mmol) in Et$_2$O (2.63 ml) at 0° C. The reaction vessel was evacuated and purged with argon. MeMgI (0.203 ml, 0.610 mmol M in Et$_2$O, 10 eq) was added dropwise to the reaction mixture which was allowed to warm to RT after addition. The reaction mixture stirred at RT for 30 minutes at which time the methyl ester was no longer present by TLC (hexanes:Et$_2$O, 2:1). Solvent was removed under reduced pressure to give a crude oil that was heated to 160° C. for 2 hours using a house vacuum. At this time the reaction was cooled to RT and diluted with Et$_2$O (5 ml) then quenched with saturated aq. NH$_4$Cl (10 ml). The aqueous layer was extracted with Et$_2$O (3×15 ml), washed with brine (15 ml), dried over MgSO$_4$ and filtered to give an oil. The crude oil was dissolved in DCM (3 ml) and added dropwise to a separate round bottom containing MgSO$_4$ (0.029 g, 0.24 mmol) and ZnBr$_2$ (0.019 g, 0.085 mmol) and stirred at RT for 8 hours. At this time the reaction mixture was quenched with saturated aq.NH$_4$Cl (10 ml) and the aqueous layer was extracted with DCM (3×15 ml). Combined organic layers were dried over MgSO$_4$, filtered and concentrated to give a crude oil that was purified by column chromatography using hexanes: Et$_2$O (20:1) to provide THC (0.011 g, 0.035 mmol), 57.3%) of slightly tan oil. [α]$^{20}_D$=−150 (c=0.1, CHCl$_3$). $^1$H NMR (500 MHz, CDCl3): δ 6.27-6.30 (m, 1H), 6.26 (d, J=1.5 Hz, 1H), 6.12 (d, J=1.6 Hz, 1H), 4.72 (s, 1H), 3.15-3.22 (m, 1H), 2.42 (td, J=7.7, 2.2 Hz, 1H), 2.12-2.18 (m, 3H), 1.87-1.94 (m, 1H), 1.67 (s, 3H), 1.64-1.69 (m, 1H), 1.50-1.56 (m, 2H), 1.40 (s, 3H), 1.37-1.43 (m, 1H), 1.25-1.32 (m, 4H), 1.08 (s, 3H), 0.86 (t, J=6.8 Hz, 3H) ppm. $^{13}$C NMR (126 MHz, CDCl$_3$): δ 154.7, 154.1, 142.8, 134.4, 123.7, 110.1, 109.7, 107.5, 77.2, 45.8, 35.5, 33.5, 31.5, 31.2, 30.6, 27.6, 25.0, 23.4, 22.5, 19.3, 14.0 ppm. HRMS m/z: [M+Na]$^+$ calculated for C$_{21}$H$_{30}$O$_2$Na 337.2138, found 337.2131.

Example 10. Compound 10 (Step 1)

A 25 mL round-bottomed flask was equipped with a stir bar, flame dried, and then cooled to RT under vacuum. The flask was put under Argon before adding (E)-3-(2,6-dimethoxy-4-pentylphenyl)-2-(3-methylbut-3-en-1-yl)hex-4-enoic acid (0.315 g, 0.811 mmol) in Ether (8.11 ml). The flask was cooled to 0° C. and methyl lithium (1.28 ml, 2.03 mmol) (1.6M in Et$_2$O) was added dropwise via syringe before warming from 0° C. to rt over 1 hour. The reaction was allowed to stir overnight at rt before being checked by TLC. Once complete, the reaction was quenched with sat NH$_4$Cl (25 mL) and the aqueous layer was extracted with DCM (3×20 mL). The combined organic layers were dried with MgSO$_4$, filtered, and concentrated. The resulting crude oil was subjected to silica gel column chromatography (9:1-4:1 Hex:EtOAc) to give (E)-4-(2,6-dimethoxy-4-pentylphenyl)-3-(3-methylbut-3-en-1-yl)hept-5-en-2-one (0.225 g, 0.582 mmol, 71.8% yield) as a colorless oil. [α]$^{20}_D$=+45.1 (c=1, CHCl$_3$). IR (neat): 2933, 2858, 1711, 1581, 1458, 1424, 1231, 1126, 974, 892, 825 cm$^{-1}$. $^1$H NMR (400 MHz, CDCl3): δ 6.30 (s, 2H), 5.76 (ddd, J=15.0, 9.6, 1.6 Hz, 1H), 5.51 (dq, J=15.2, 6.4 Hz, 1H), 4.69 (s, 1H), 4.65 (s, 1H), 3.96 (t, J=10.2 Hz, 1H), 3.78 (s, 6H), 3.25 (td, J=10.9, 3.1 Hz, 1H), 2.48 (t, J=7.8 Hz, 2H), 1.83-1.95 (m, 2H), 1.76-1.82 (m, 1H), 1.75 (s, 3H), 1.68 (s, 3H), 1.63-1.67 (m, 1H), 1.61 (dd, J=6.2, 1.6 Hz, 3H), 1.52-1.58 (m, 2H), 1.27-1.33 (m, 4H), 0.87 ppm (t, J=6.8 Hz, 3H) ppm. $^{13}$C NMR (101 MHz, CDCl$_3$): δ 213.2, 157.5, 145.7, 142.9, 131.2, 126.7, 115.8, 109.9, 104.7, 55.7, 54.7, 42.1, 36.4, 35.8, 31.6, 30.9, 29.4, 28.8, 22.5, 22.3, 17.9, 14.0 ppm. HRMS m/z: [M+H]$^+$ calculated for C$_{25}$H$_{39}$O$_3$ 387.2894, found 387.2892.

Example 11. Compound 10 (Step 2)

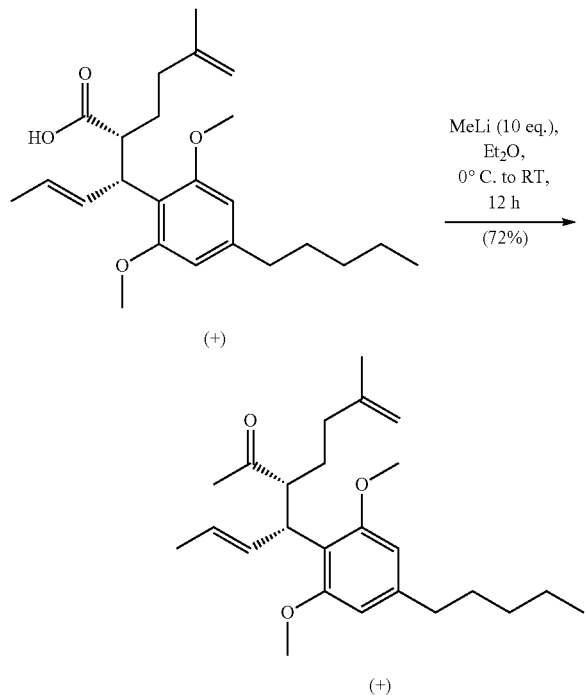

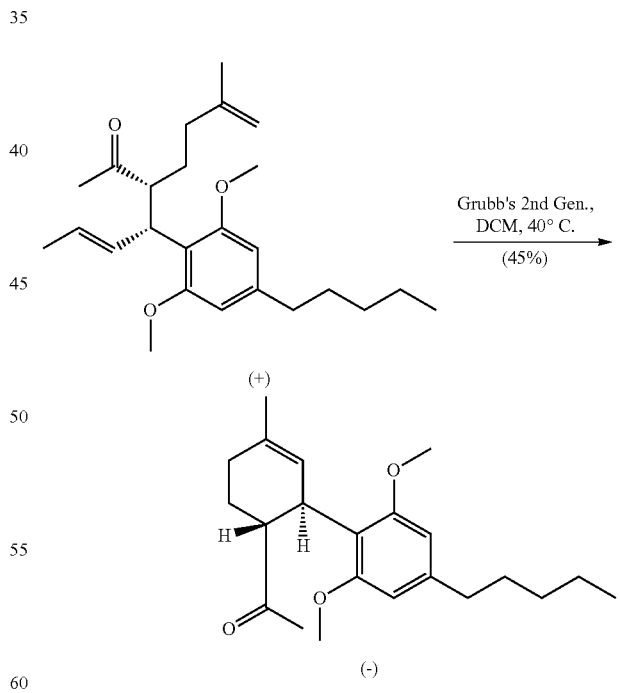

In a 15 mL round bottom flask equipped with a stir bar was (E)-4-(2,6-dimethoxy-4-pentylphenyl)-3-(3-methylbut-3-en-1-yl)hept-5-en-2-one (0.225 g, 0.582 mmol) in DCM (6.5 ml) (Degassed with N$_2$ flow for 15 min). To this solution Grubb's 2nd generation catalyst (0.006 g, 0.007 mmol) was added and the vessel was sealed with a septum and vacuum purged with argon. The reaction mixture stirred for 10 h at 40° C. Another portion of the catalyst (0.006 g, 0.007 mmol) was added to the reaction mixture and it continued to stir for 5 hours at 40° C. The solvent was removed under vacuum and the crude material was loaded onto a silica gel column and purified using Hex/EtOAc (14:1-9:1) to afford 1-(2',6'-dimethoxy-5-methyl-4'-pentyl-1,2,3,4-tetrahydro-[1,1'-biphenyl]-2-yl)ethanone (0.031 g, 0.090 mmol, 69.6% yield) as a tan oil. $[\alpha]^{20}_D$=−146.1 (c=1, CHCl$_3$). IR (neat): 3007, 2959, 2929, 2858, 1707, 1584, 1458, 1424, 1234, 1119, 828, 758, 672, 601 cm$^{-1}$. $^1$H NMR (400 MHz, CDCl$_3$): δ 6.32 (s, 2H), 5.13 (s, 1H), 4.10-4.19 (m, 1H), 3.72 (s, 6H), 3.25 (ddd, J=12.6, 10.3, 2.9 Hz, 1H), 2.51 (t, J=7.4 Hz, 2H), 2.05-2.17 (m, 1H), 1.93-2.02 (m, 1H), 1.85-1.93 (m, 4H), 1.70-1.84 (m, 1H), 1.64 (s, 3H), 1.53-1.62 (m, 2H), 1.24-1.37 (m, 4H), 0.88 (t, J=7.0 Hz, 3H) ppm. $^{13}$C NMR (101 MHz, CDCl$_3$): δ 213.5, 158.4, 142.8, 131.0, 124.8, 117.2, 104.9, 55.9, 51.1, 36.4, 34.6, 31.6, 31.0, 29.5, 28.6, 26.5, 23.3, 22.5, 14.0 ppm. HRMS m/z: [M+H]$^+$ calculated for C$_{22}$H$_{33}$O$_3$ 345.2424, found 345.2427.

Example 12. Compound 11

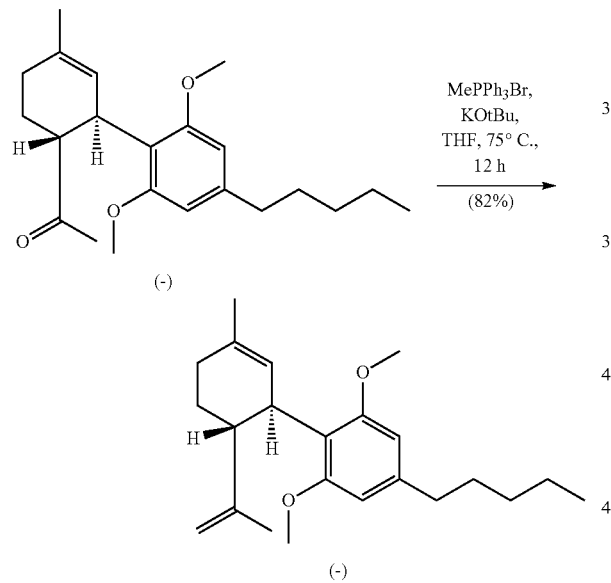

In a 10 mL round-bottomed flask equipped with a stir bar was added 1-(2',6'-dimethoxy-5-methyl-4'-pentyl-1,2,3,4-tetrahydro-[1,1'-biphenyl]-2-yl)ethanone (0.022 g, 0.064 mmol) and bromo(methyl)triphenylphosphorane (0.027 g, 0.077 mmol) in THF (1.0 mL) under argon. The solution was stirred at room temperature before adding potassium tert-butoxide (8.6 mg, 0.077 mmol) in THF (0.30 ml) dropwise. The mixture stirred until full consumption of the starting material was observed (TLC, 12 h). The solvent was evaporated and the residue was diluted with hexane to precipitate triphenylphosphine oxide. After filtration, a 10% aqueous acetic acid solution (10 mL) and hexane (15 mL) were added and the aqueous layer extracted with hexane (3×10 mL). The combined organic layers were washed with sat. NaHCO$_3$, dried with MgSO$_4$, filtered and solvent was removed under reduced pressure. The crude product was purified by column chromatography using hexanes:EtOAc (6:1) to provide (1R, 2R)-2',6'-dimethoxy-5-methyl-4'-pentyl-2-(prop-1-en-2-yl)-1,2,3,4-tetrahydro-1,1'-biphenyl (18 mg, 0.052 mmol, 82%) as a light yellow oil. $[\alpha]^{20}_D$=−158.2 (c=1, CHCl$_3$). $^1$H NMR (400 MHz, CDCl$_3$): δ 6.32 (s, 2H), 5.20 (s, 1H), 4.42-4.45 (m, 1H), 4.40-4.42 (m, 1H), 3.94-4.02 (m, 1H), 3.72 (s, 6H), 2.89 (td, J=10.5, 4.7 Hz, 1H), 2.52 (t, J=7.8 Hz, 2H), 2.11-2.25 (m, 1H), 1.93-2.02 (m, 1H), 1.69-1.78 (m, 2H), 1.66 (s, 3H), 1.56-1.63 (m, 5H), 1.29-1.38 (m, 4H), 0.89 (t, J=6.8 Hz, 3H) ppm. $^{13}$C NMR (101 MHz, CD3OD): δ 158.7, 149.0, 141.7, 130.2, 126.1, 118.5, 108.9, 104.4, 54.8, 45.2, 36.0, 36.0, 31.4, 30.9, 30.4, 29.5, 22.3, 22.2, 18.0, 13.1 ppm. HRMS m/z: [M+H]$^+$ calculated for C$_{23}$H$_{35}$O$_2$ 343.2632, found 343.2632.

Example 13. Cannabidiol (CBD)

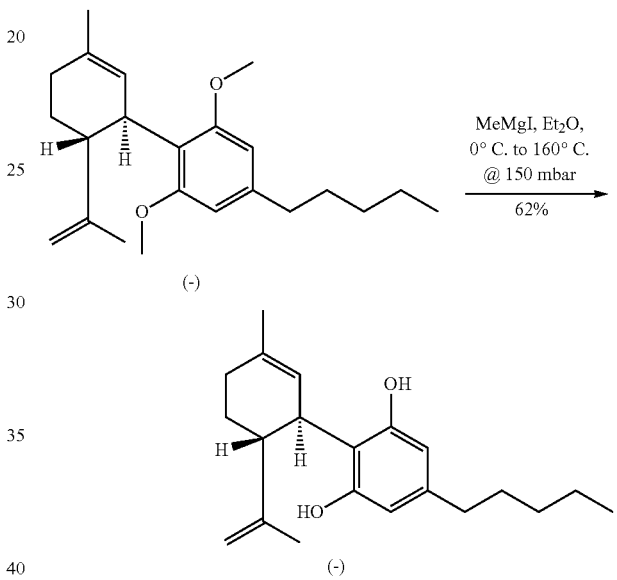

In a 15 mL round-bottomed flask was 2',6'-dimethoxy-5-methyl-4'-pentyl-2-(prop-1-en-2-yl)-1,2,3,4-tetrahydro-1,1'-biphenyl (0.050 g, 0.15 mmol) in anhydrous ether (0.487 mL) under argon at room temperature. Methylmagnesium iodide (0.195 mL, 0.584 mmol, 3M in Et$_2$O) was added dropwise and the solution was heated to 160° C. for 1.5 hours under reduced pressure (house vacuum). The reaction mixture was cooled to room temperature, diluted with Et$_2$O (5 mL) and quenched with sat. NH$_4$Cl (5 mL). The aqueous layer was extracted with Et$_2$O (3×15 ml), dried over Na$_2$SO$_4$, filtered and concentrated to give a tan oil. The crude product was purified by column chromatography using hexanes:ether (15:1) to provide CBD (28.4 mg, 0.905 mmol, 62%) as a light-yellow oil. $[\alpha]^{20}_D$=−131.3 (c=1, EtOH). $^1$HNMR (400 MHz, CDCl$_3$): δ 6.07-6.36 (m, 2H), 5.95 (br s, 1H), 5.54 (s, 1H), 4.60-4.77 (m, 2H), 4.53 (s, 1H), 3.78-3.87 (m, 1H), 2.41 (t, J=7.4 Hz, 2H), 2.33-2.38 (m, J=3.5 Hz, 1H), 2.14-2.29 (m, 1H), 2.01-2.12 (m, 1H), 1.77 (s, 3H), 1.68-1.85 (m, 2H), 1.63 (s, 3H), 1.53 (app. quin, J=7.4 Hz, 2H), 1.20-1.35 (m, 4H), 0.85 (t, J=7.0 Hz, 3H) ppm. $^{13}$C NMR (CD$_3$OD, 101 MHz): δ 156.0, 148.8, 141.3, 132.9, 125.8, 114.5, 109.1, 106.9, 45.0, 36.0, 35.2, 31.2, 30.6, 30.3, 29.4, 22.3, 22.2, 18.1, 13.0. HRMS m/z: [M+H]$^+$ calculated for C$_{21}$H$_{31}$O$_2$ 315.2319, found 315.2318.

Example 14. 5-methylhex-5-enoic acid and 2,2,2-trifluoroethyl 5-methylhex-5-enoate

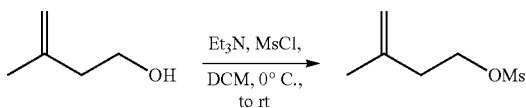

In a 500 mL round-bottomed flask equipped with a stir bar was added 3-methyl-3-buten-1-ol (11.7 mL, 116 mmol) in dry DCM (200 mL) to give a clear colorless solution. NEt$_3$ (17.7 mL, 128 mmol) was added and the solution was cooled to 0° C. Methanesulfonyl chloride (9.96 mL, 128 mmol) was then added dropwise over 5 min then stirred for 1 h at 0° C. The reaction mixture was diluted with DCM (200 mL), washed with 1M HCl (200 mL), satd. NaHCO$_3$ (250 mL) and brine (200 mL). The combined organic layer was dried over Na$_2$SO$_4$, filtered, and the solvent was removed under reduced pressure to give an orange-yellow oil that was used in the next step without further purification.

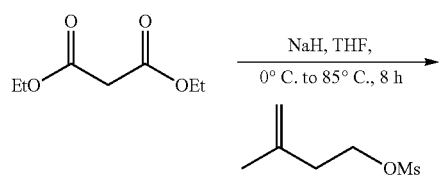

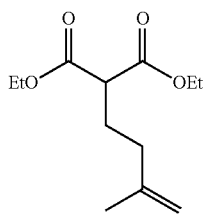

In a 1 L round-bottomed flask equipped with a stir bar was added sodium hydride (7.10 g, 178 mmol) and sodium iodide (2.41 g, 16.1 mmol) in THF (334 mL) at 0° C. To this solution diethyl malonate (24.6 mL, 161 mmol) was added dropwise. The suspension was heated to reflux for 30 min before 3-methyl-3-buten-1-yl methanesulfonate (31.8 g, 194 mmol) was added dropwise over 10 min. The resulting reaction mixture was heated for 16 h at 85° C. Once complete (TLC), the reaction mixture was cooled to rt and quenched by the addition of satd. aq. NH$_4$Cl (600 mL). The mixture was extracted with EtOAc (3×300 mL), washed with brine (400 mL), dried over Na$_2$SO$_4$, filtered, and concentrated to give a yellow oil. The crude product was purified by silica gel column chromatography using hexanes/EtOAc (19:1) to afford diethyl 2-(3-methyl-3-buten-1-yl)malonate (34.4 g, 151 mmol, 93% yield). $^1$H NMR (400 MHz, CDCl$_3$): δ 4.73 (s, 1H), 4.67 (s, 1H), 4.17 (q, J=7.0 Hz, 4H), 3.27-3.34 (m, 1H), 2.00-2.05 (m, 4H), 1.69 (s, 3H), 1.24 ppm (t, J=7.0 Hz, 6H). $^{13}$C NMR (CDCl3, 101 MHz): δ 169.4, 144.0, 111.1, 61.2, 51.3, 35.2, 26.6, 22.1, 14.0 ppm.

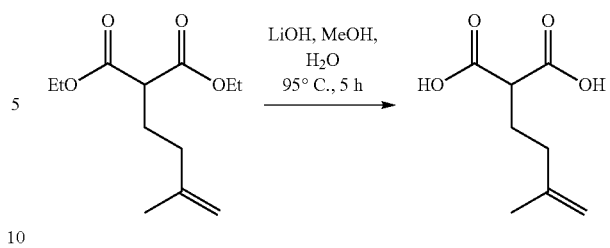

In a 250 mL round-bottomed flask equipped with a stir bar was added diethyl 2-(3-methyl-3-buten-1-yl)malonate (9.92 g, 43.4 mmol) in a mixture of water and methanol (1:1, 100.6 mL). Lithium hydroxide monohydrate (9.11 g, 217 mmol) was added and the mixture was heated to 95° C. for 5 h. The reaction mixture was cooled to rt and then diluted with 100 mL of water, acidified with concentrated HCl to a pH of 1 and the aqueous layer was extracted with dichloromethane (4×100 mL). The combined organic layers were dried over Na$_2$SO$_4$, filtered, and the solvent evaporated. The product 2-(3-methyl-3-buten-1-yl)malonic acid was obtained as a white solid which was used without further purification or characterization.

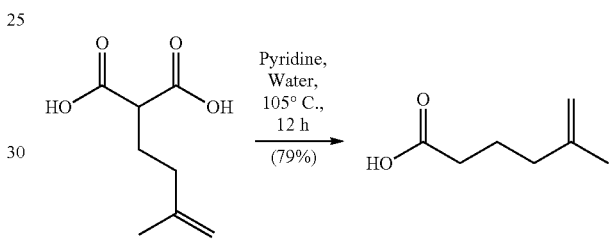

In a 25 mL round-bottomed flask equipped with a stir bar was added 2-(3-methyl-3-buten-1-yl)malonic acid (2.25 g, 12.8 mmol) dissolved in pyridine (5.29 mL) and water (0.265 mL). The mixture was heated to reflux for 14 h then cooled to rt. Once cool, pyridine was removed under reduced pressure and the residue was dissolved in 20 mL of water and acidified with concentrated HCl to a pH of 1. The aqueous solution was extracted with DCM (3×40 mL), dried over Na$_2$SO$_4$, filtered, and the solvent removed under reduced pressure to give yellow-orange oil. The crude product was purified by silica gel column chromatography using hexanes/EtOAc (30:1 to 1:1) to afford 5-methylhex-5-enoic acid (1.32 g, 10.2 mmol, 79% yield) as clear light yellow oil. $^1$H NMR (400 MHz, CDCl$_3$): δ 11.06-12.19 (m, 1H), 4.73 (s, 1H), 4.68 (d, J=0.8 Hz, 1H), 2.34 (t, J=7.4 Hz, 2H), 2.05 (t, J=7.4 Hz, 2H), 1.77 (app. quin, J=7.5 Hz, 2H), 1.70 (s, 3H) ppm: δ 180.4, 144.5, 110.7, 36.9, 33.4, 22.4, 22.1 ppm.

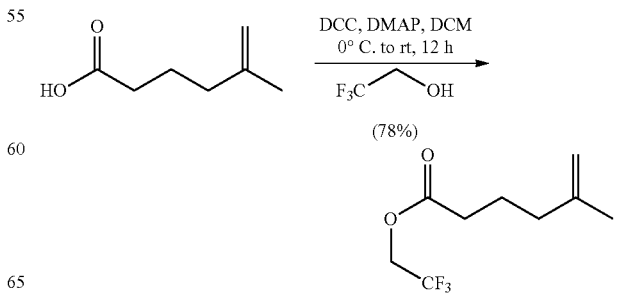

In a 1 L round-bottomed flask equipped with a stir bar was added DCC (16.8 g, 82.2 mmol) and DMAP (1.81 g, 14.8 mmol) in DCM (370 mL) at 0° C. To this cold solution 5-methylhex-5-enoic acid (9.91 mL, 74.1 mmol) was added along with 2,2,2-trifluoroethanol (8 mL, 0.1 mol). The reaction continued to stir at 0° C. for 30 min before warming to rt where it continued to stir for an additional 12 h. At this point acetic acid (1.1 mL, 19 mmol) was added to the reaction mixture and it stirred for an additional 1 h. The reaction mixture was then filtered through a pad of Celite and rinsed with an additional 100 mL of DCM. The filtrate was washed with 1N HCl (150 mL), neutralized with NaHCO$_3$ (150 mL) then dried over Na$_2$SO$_4$, filtered and concentrated to give an oily solid. The crude material was purified by short-path vacuum distillation (50-55° C. at 4 mm Hg) to give 2,2,2-trifluoroethyl 5-methyl-5-hexenoate (12.2 g, 57.1 mmol, 78%) as a clear colorless oil. IR (neat): 2936, 2858, 2121, 1763, 1454, 1417, 1286, 1167, 1137, 981, 895 cm$^{-1}$. 1H NMR (400 MHz, CDCl$_3$): δ 4.69 (s, 1H), 4.63 (s, 1H), 4.40 (q, J=8.3 Hz, 2H), 2.35 (t, J=7.4 Hz, 2H), 1.97-2.03 (m, 2H), 1.75 (quin, J=7.5 Hz, 2H), 1.65 ppm (s, 3H).

It is also to be understood that the following claims are intended to cover all of the generic and specific features of the invention herein described, and all statements of the scope of the invention that, as a matter of language, might be said to fall therebetween.

What is claimed is:

1. A process for the preparation of a compound of formula (I-a),

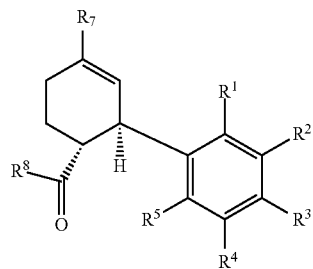

(I-a)

the process comprising the steps of:
(a) converting a compound of formula (II-a) to a compound of formula (III-a), and

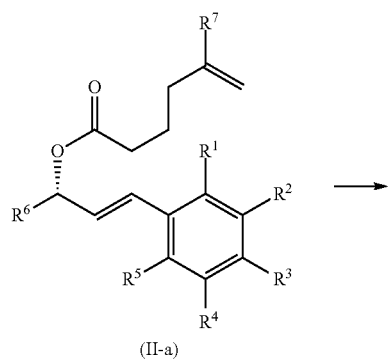

(II-a)

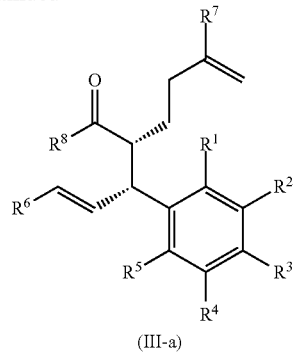

(III-a)

(b) converting the compound of formula (III-a) to the compound of formula (I-a),
wherein
$R^1$ and $R^5$ at each occurrence are independently hydroxyl or a protected hydroxyl group;
$R^2$ and $R^4$ at each occurrence are independently hydrogen or $C_1$-$C_{10}$ alkyl;
$R^3$ at each occurrence is independently $C_1$-$C_{10}$ alkyl;
$R^6$ and $R^7$ at each occurrence are independently hydrogen or $C_1$-$C_{10}$ alkyl;
$R^8$ at each occurrence is independently hydroxyl, $C_1$-$C_{10}$ alkyl, or $C_1$-$C_{10}$ alkoxy;
wherein $R^2$, $R^3$, $R^4$, $R^6$, $R^7$, and $R^8$ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle; and
wherein step (b) is performed in a solvent selected from the group consisting of tetrahydrofuran and toluene.

2. The process of claim 1, further comprising the step of reacting a compound of formula (IV-a) with a compound of formula (V) to produce the compound of formula (II-a)

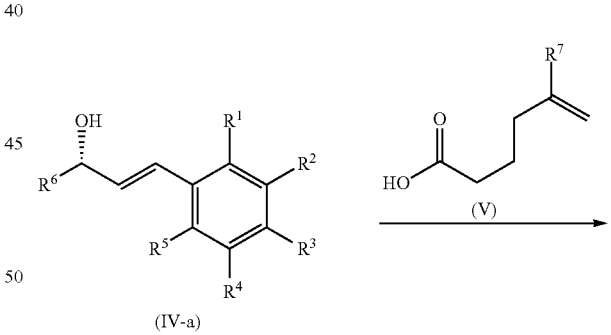

(IV-a)  (V)

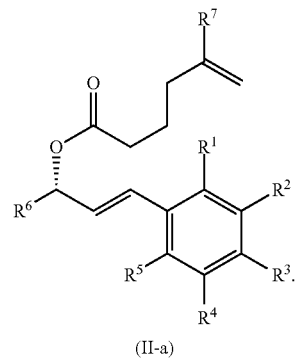

(II-a)

3. The process of claim 2, further comprising the step of converting a compound of formula (VI) to the compound of formula (IV-a)

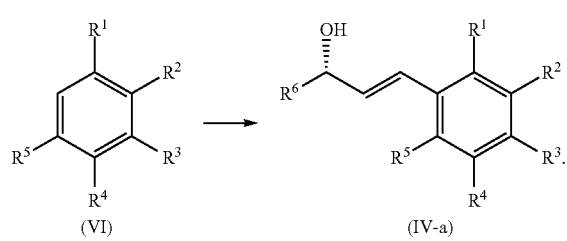

4. The process of claim 3, further comprising the steps of converting the compound of formula (VI) to a compound of formula (IV'), and reducing the compound of formula (IV') to the compound of formula (IV-a)

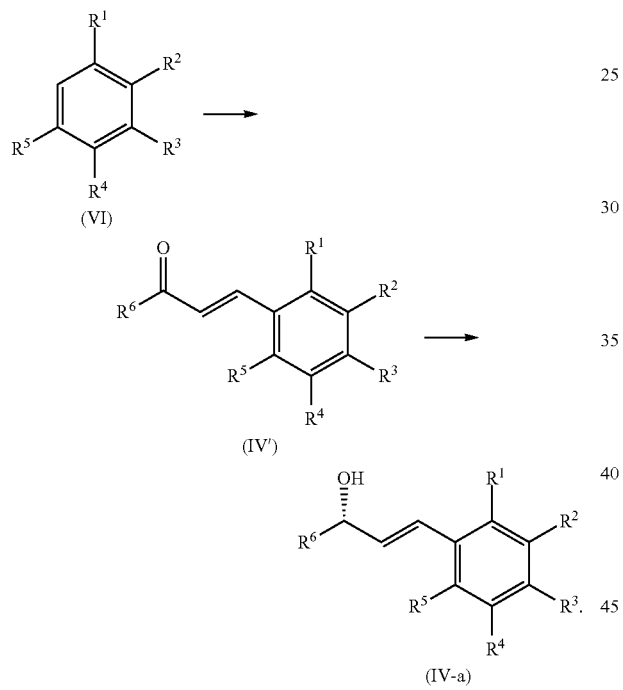

5. The process of claim 1, wherein step (a) comprises mixing potassium bis(trimethylsilyl)amide (KHMDS) with the compound of formula (II-a).

6. The process of claim 1, wherein $R^3$ is —$(CH_2)_4$—$CH_3$.

7. The process of claim 1, wherein $R^1$ and $R^5$ are —$OCH_3$.

8. The process of claim 1, wherein $R^6$ and $R^7$ are each —$CH_3$.

9. The process of claim 1, wherein $R^8$ is hydroxyl, —$CH_3$, or —$OCH_3$.

10. The process of claim 1, wherein step (b) comprises mixing the compound of formula (III-a) with (1,3-Bis(2,4,6-trimethylphenyl)-2-imidazolidinylidene)dichloro(phenylmethylene)(tricyclohexylphosphine)ruthenium.

11. A process for the preparation of a compound of formula (I), a racemate or a stereoisomer thereof,

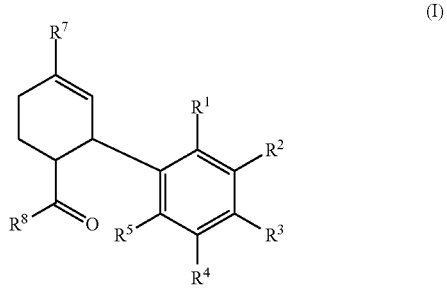

the process comprising the steps of:
(a) converting a compound of formula (II) to a compound of formula (III), and

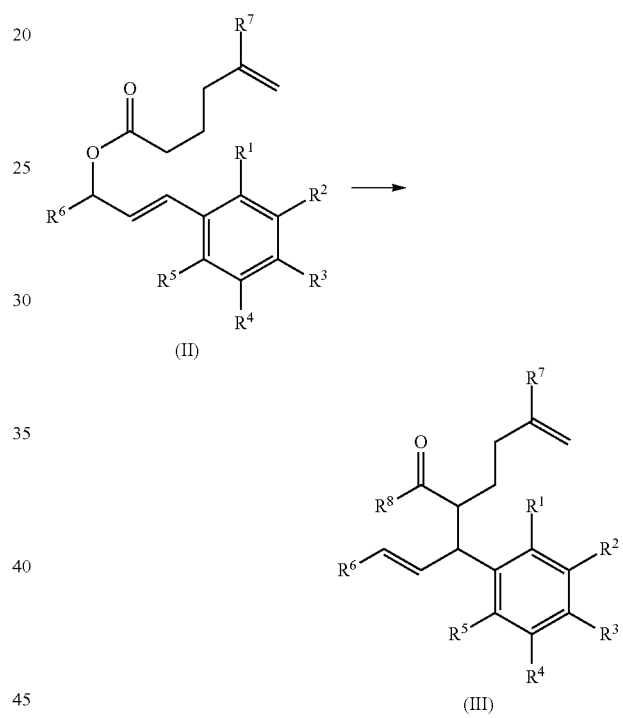

(b) converting the compound of formula (III) to the compound of formula (I),
further comprising the step of reacting a compound of formula (IV) with a compound of formula (V) to produce the compound of formula (II)

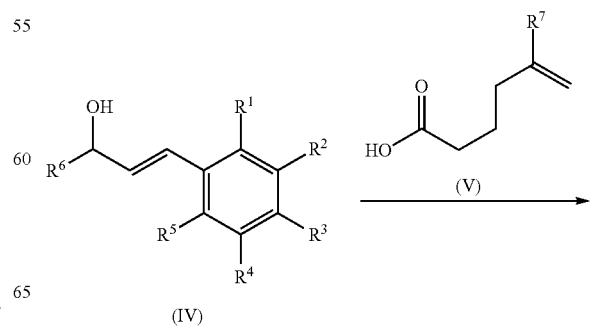

49

-continued

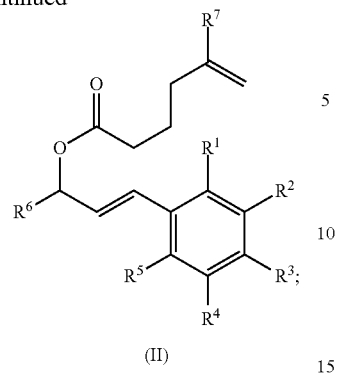

(II)

further comprising the steps of converting a compound of formula (VI) to a compound of formula (IV'), and reducing the compound of formula (IV') to the compound of formula (IV)

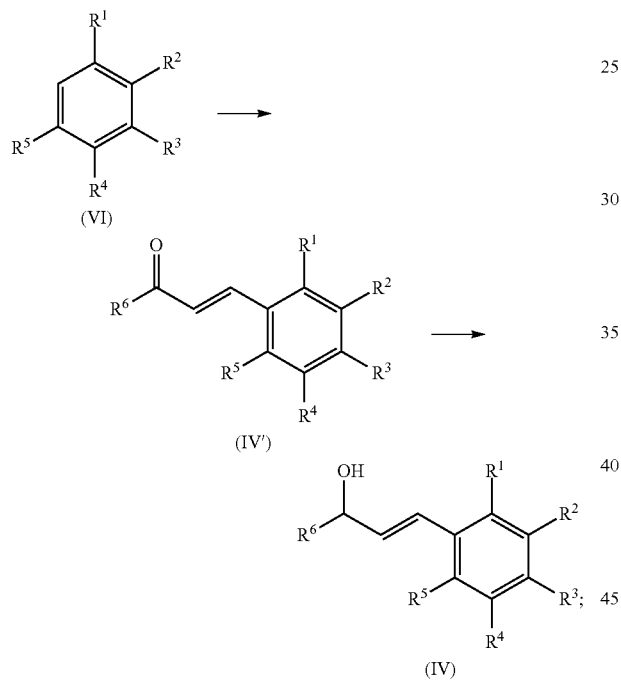

wherein
$R^1$ and $R^5$ at each occurrence are independently hydroxyl or a protected hydroxyl group;
$R^2$ and $R^4$ at each occurrence are independently hydrogen or $C_1$-$C_{10}$ alkyl;
$R^3$ at each occurrence is independently $C_1$-$C_{10}$ alkyl;
$R^6$ and $R^7$ at each occurrence are independently hydrogen or $C_1$-$C_{10}$ alkyl;
$R^8$ at each occurrence is independently hydroxyl, $C_1$-$C_{10}$, alkyl, or $C_1$-$C_{10}$, alkoxy;
wherein $R^2$, $R^3$, $R^4$, $R^6$, $R^7$, and $R^8$ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle.

50

12. A process for the preparation of a compound of formula (I), a racemate or a stereoisomer thereof,

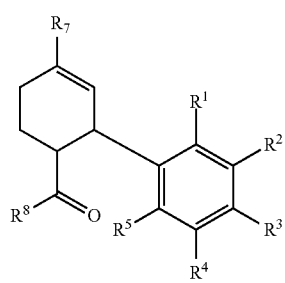

the process comprising the steps of:
(a) converting a compound of formula (II) to a compound of formula (III), and

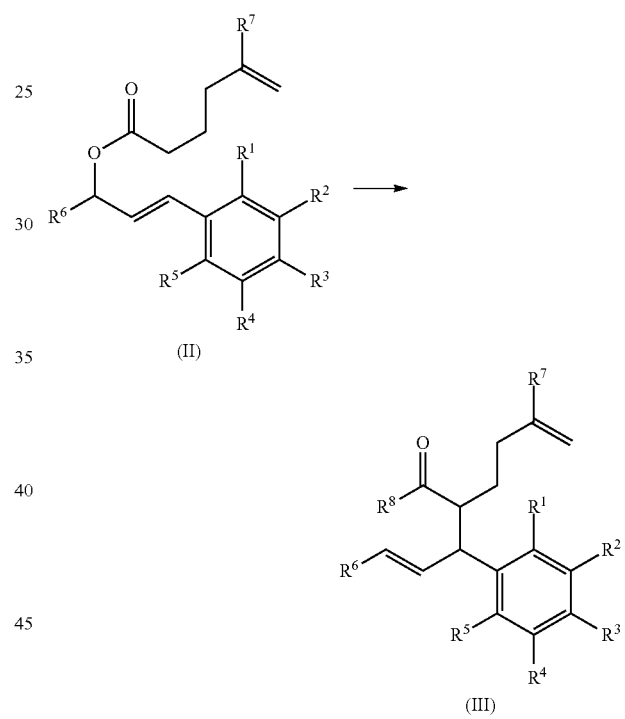

(b) converting the compound of formula (III) to the compound of formula (I),
wherein
$R^1$ and $R^5$ at each occurrence are independently hydroxyl or a protected hydroxyl group;
$R^2$ and $R^4$ at each occurrence are independently hydrogen or $C_1$-$C_{10}$ alkyl;
$R^3$ at each occurrence is independently $C_1$-$C_{10}$ alkyl;
$R^6$ and $R^7$ at each occurrence are independently hydrogen or $C_1$-$C_{10}$ alkyl;
$R^8$ at each occurrence is independently hydroxyl, $C_1$-$C_{10}$ alkyl, or $C_1$-$C_{10}$ alkoxy;
wherein $R^2$, $R^3$, $R^4$, $R^6$, $R^7$, and $R^8$ at each occurrence are independently optionally substituted with one or more substituents selected from the group consisting of alkenyl, alkynyl, alkoxycarbonyl, alkylcarbonyl, halogen, cyano, carboxyl, hydroxyl, protected hydroxyl, amino, oxo, aryl, arylcarbonyl, cycloalkyl, heteroaryl, and heterocycle;

wherein step (a) comprises mixing potassium bis(trimethylsilyl)amide (KHMDS) with the compound of formula (II).

* * * * *